United States Patent
Sato et al.

(10) Patent No.: US 7,585,926 B2
(45) Date of Patent: Sep. 8, 2009

(54) FLUORINE-CONTAINING COMPOUND HAVING HYDROLYZABLE METAL ALKOXIDE MOIETY, CURABLE FLUORINE-CONTAINING POLYMER PREPARED FROM THE SAME COMPOUND, AND CURABLE FLUORINE-CONTAINING RESIN COMPOSITION COMPRISING THE SAME POLYMER

(75) Inventors: Kazuyuki Sato, Settsu (JP); Tsuyoshi Itagaki, Settsu (JP); Yasuo Itami, Settsu (JP)

(73) Assignee: Daikin Industries, Ltd., Osaka (JP)

(*) Notice: Subject to any disclaimer, the term of this patent is extended or adjusted under 35 U.S.C. 154(b) by 38 days.

(21) Appl. No.: 11/661,977

(22) PCT Filed: Aug. 25, 2005

(86) PCT No.: PCT/JP2005/015452
§ 371 (c)(1),
(2), (4) Date: Mar. 6, 2007

(87) PCT Pub. No.: WO2006/027958
PCT Pub. Date: Mar. 16, 2006

(65) Prior Publication Data
US 2008/0108767 A1 May 8, 2008

(30) Foreign Application Priority Data
Sep. 9, 2004 (JP) .............................. 2004-262841

(51) Int. Cl.
C08F 30/04 (2006.01)
C08F 130/04 (2006.01)
C08F 230/04 (2006.01)

(52) U.S. Cl. .................. 526/240; 526/241; 526/245; 526/247; 526/250; 526/279; 526/320

(58) Field of Classification Search ............ 526/240, 526/245, 247, 250
See application file for complete search history.

(56) References Cited

U.S. PATENT DOCUMENTS

| 5,401,818 | A | * | 3/1995 | Oka et al. ..................... 526/247 |
| 6,183,872 | B1 | * | 2/2001 | Tanaka et al. ................ 428/429 |
| 6,811,854 | B1 | * | 11/2004 | Sato et al. .................... 428/141 |
| 2003/0235933 | A1 | | 12/2003 | Rantala et al. |
| 2004/0115341 | A1 | * | 6/2004 | Rantala et al. .............. 427/123 |

FOREIGN PATENT DOCUMENTS

JP 5-17535 A 1/1993
JP 2001-353817 A 12/2001

OTHER PUBLICATIONS

Machine translation of Dainippon Ink and Chemicals, Inc., JP 2001-353817, Dec. 2001.*

* cited by examiner

Primary Examiner—Marc S Zimmer
Assistant Examiner—Nicole M Buie
(74) Attorney, Agent, or Firm—Sughrue Mion, PLLC

(57) ABSTRACT

There is provided a material which is free from fading into white due to surface scattering and is useful as a laminated article having excellent adhesion and practical low reflection. A fluorine-containing compound which has a hydrolyzable metal alkoxide moiety and is represented by the formula (1):

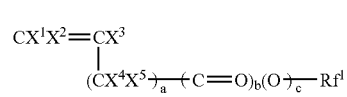

wherein $X^1$ and $X^2$ are the same or different, and each is H or F; $X^3$ is H, F, $CH_3$ or $CF_3$; $X^4$ and $X^5$ are the same or different, and each is H, F or $CF_3$; $Rf^1$ is a fluorine-containing alkyl group having 1 to 40 carbon atoms or a fluorine-containing alkyl group having 2 to 100 carbon atoms and ether bond, which is an organic group in which 1 to 3 hydrogen atoms are replaced by $Y^1$ where $Y^1$ is a functional group having, at its end, at least one hydrolyzable metal alkoxide moiety having 1 to 10 carbon atoms; a is 0 or an integer of 1 to 3; b and c are the same or different, and each is 0 or 1, a curable fluorine-containing polymer obtained from the above-mentioned compound, and a curable fluorine-containing resin composition comprising the polymer.

10 Claims, 2 Drawing Sheets

FLUORINE-CONTAINING COMPOUND HAVING HYDROLYZABLE METAL ALKOXIDE MOIETY, CURABLE FLUORINE-CONTAINING POLYMER PREPARED FROM THE SAME COMPOUND, AND CURABLE FLUORINE-CONTAINING RESIN COMPOSITION COMPRISING THE SAME POLYMER

TECHNICAL FIELD

The present invention relates to a novel fluorine-containing compound and polymer having a hydrolyzable metal alkoxide moiety, and a curable fluorine-containing resin composition prepared using the polymer.

BACKGROUND ART

In order to enhance visibility of an image of liquid crystal displays (LCD) and the like, measures to inhibit a reflection on the surface thereof are taken. One of such measures is to provide, on the surface, a light scattering layer having a fine uneven structure giving an anti-glaring property. However, when the light scattering layer is provided on the surface of LCD, there is a demerit such that surface scattering arises and when a black color is displayed, the displayed picture becomes whitish, namely, so-called "fading into white color" arises, which results in lowering of an image contrast.

For making improvement in reducing this "fading into white color", there is a method of imparting a reflection reducing ability to prevent lowering of an image contrast by providing, on a surface of a resin coating layer having a fine uneven structure, a coating layer having a refractive index lower than that of the resin coating layer (for example, JP-A10-201043 and JP-A-2003-344614).

However, with respect to a coating layer to be provided on a surface of a conventional resin coating layer having a fine uneven structure, there have been proposed only materials having a high refractive index (for example, not less than 1.40). As a result, a displayed image contrast is lowered, and also durability is poor since such a coating layer is lacking in adhesion to the light scattering layer which is a substrate.

Such being the case, laminating materials having practical anti-glaring property and low reflection in which improvements are made in solving the mentioned problems are desired.

DISCLOSURE OF INVENTION

An object of the present invention is to provide a material which is useful for a laminated article having a practical low reflection, keeps an anti-glaring property, is free from "fading into white color" attributable to surface scattering and is excellent in adhesion.

Namely, the present invention relates to a curable fluorine-containing polymer (hereinafter referred to as "the first polymer") having a hydrolyzable metal alkoxide moiety which has a number average molecular weight of from 500 to 1,000,000 and is represented by the formula (2):

 (2)

wherein the structural unit M is a structural unit which is derived from a fluorine-containing ethylenic monomer having a hydrolyzable metal alkoxide moiety and is represented by the formula (M):

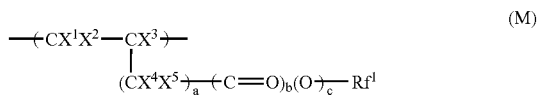 (M)

in which $X^1$ and $X^2$ are the same or different, and each is H or F; $X^3$ is H, F, $CH_3$ or $CF_3$; $X^4$ and $X^5$ are the same or different, and each is H, F or $CF_3$; $Rf^1$ is a fluorine-containing alkyl group having 1 to 40 carbon atoms or a fluorine-containing alkyl group having 2 to 100 carbon atoms and ether bond, which is an organic group in which 1 to 3 hydrogen atoms are replaced by $Y^1$ where $Y^1$ is a functional group containing, at its end, at least one hydrolyzable metal alkoxide moiety and having 1 to 50 carbon atoms; a is 0 or an integer of 1 to 3; b and c are the same or different, and each is 0 or 1, the structural unit N is a structural unit derived from a fluorine-containing ethylenic monomer and represented by the formula (N):

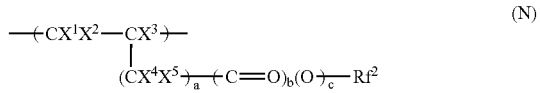 (N)

in which $X^1$ and $X^2$ are the same or different, and each is H or F; $X^3$ is H, F, $CH_3$ or $CF_3$; $X^4$ and $X^5$ are the same or different, and each is H, F or $CF_3$; $Rf^2$ is a fluorine-containing alkyl group having 1 to 40 carbon atoms or a fluorine-containing alkyl group having 2 to 100 carbon atoms and ether bond, which is an organic group in which 1 to 3 hydrogen atoms are replaced by $Y^2$ where $Y^2$ is a monovalent organic group having 2 to 10 carbon atoms and containing, at its end, an ethylenic carbon-carbon double bond; a is 0 or an integer of 1 to 3; b and c are the same or different, and each is 0 or 1, the structural unit A is a structural unit derived from a monomer being copolymerizable with the fluorine-containing ethylenic monomers providing the structural units represented by the formulae (M) and (N), and the structural units M, N and A are contained in amounts of from 0.1 to 100% by mole, from 0 to 99.9% by mole and from 0 to 99.9% by mole, respectively.

Further the present invention relates to a curable fluorine-containing polymer (hereinafter referred to as "the second polymer") having a hydrolyzable metal alkoxide moiety which has a number average molecular weight of from 500 to 1,000,000 and is represented by the formula (2-1):

 (2-1)

wherein the structural unit M is a structural unit which is derived from a fluorine-containing ethylenic monomer having a hydrolyzable metal alkoxide moiety and is represented by the above-described formula (M), the structural unit N is a structural unit which is derived from a fluorine-containing ethylenic monomer and is represented by the above-described formula (N), the structural unit A1 is a structural unit represented by the formula (A1):

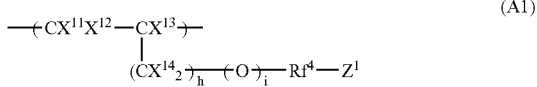

in which $X^{11}$, $X^{12}$ and $X^{13}$ are the same or different, and each is H or F; $X^{14}$ is H, F or $CF_3$; h is 0 or an integer of 1 or 2; i is 0 or 1; $Rf^4$ is a fluorine-containing divalent alkylene group having 1 to 40 carbon atoms or a fluorine-containing divalent alkylene group having 2 to 100 carbon atoms and ether bond; $Z^1$ is a group selected from the group consisting of —OH, —$CH_2OH$, —COOH, a carboxylic acid derivative, —$SO_3H$, a sulfonic acid derivative, an epoxy group and a cyano group, the structural unit A2 is a structural unit represented by the formula (A2):

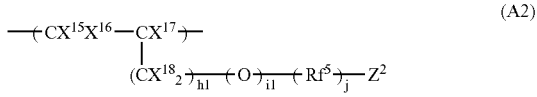

in which $X^{15}$, $X^{16}$ and $X^{18}$ are the same or different, and each is H or F; $X^{17}$ is H, F or $CF_3$; h1, i1 and j are the same or different, and each is 0 or 1; $Z^2$ is H, F, Cl or a linear or branched perfluoroalkyl group having 1 to 16 carbon atoms; $Rf^5$ is a fluorine-containing divalent alkylene group having 1 to 20 carbon atoms or a fluorine-containing divalent alkylene group having 2 to 100 carbon atoms and ether bond, the structural units M, N, A1 and A2 are contained in amounts of from 0.1 to 90% by mole, from 0 to 99.9% by mole, from 0 to 99.9% by mole and from 0 to 99.9% by mole, respectively, and N+A1+A2 is contained in an amount of from 10 to 99.9% by mole.

In any of the curable fluorine-containing polymers, it is preferable that at least one of $Y^1$ is bonded to the end of $Rf^1$, and further in the second polymer, it is preferable that at least one of $Y^2$ is bonded to the end of $Rf^2$.

In the first and second polymers represented by the formulae (2) and (2-1), respectively, the structural unit M is preferably a structural unit M1 derived from a fluorine-containing ethylenic monomer and represented by the formula (M1):

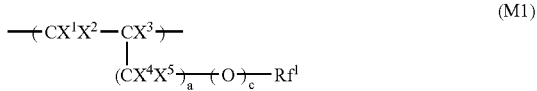

wherein $X^1$, $X^2$, $X^3$, $X^4$, $X^5$, $Rf^1$, a and c are as defined above.

Further the structural unit M is preferably a structural unit M2 derived from a fluorine-containing ethylenic monomer and represented by the formula (M2):

wherein $Rf^1$ is as defined above, or a structural unit M3 derived from a fluorine-containing ethylenic monomer and represented by the formula (M3):

wherein $Rf^1$ is as defined above.

Also in any of the curable fluorine-containing polymers, it is preferable that $Rf^1$ is one represented by the formula:

—D—Ry wherein —D— is a fluoroether unit represented by the formula (D):

in which n is an integer of 1 to 20; R is at least one selected from fluorine-containing divalent alkylene groups having 1 to 5 carbon atoms where at least one of hydrogen atoms is replaced by fluorine atom, and R may be the same or different when n is not less than two; Ry is a hydrocarbon group having 1 to 39 carbon atoms where a part or the whole of hydrogen atoms may be replaced by fluorine atoms, or a hydrocarbon group having 1 to 99 carbon atoms and ether bond where a part or the whole of hydrogen atoms may be replaced by fluorine atoms, which is an organic group in which 1 to 3 hydrogen atoms are replaced by $Y^1$ ($Y^1$ is as defined above), and more specifically Ry is preferably a group represented by the formula (Ry):

—O—$Ry^1$     (Ry)

wherein $Ry^1$ is an organic-inorganic complex radical represented by the formula:

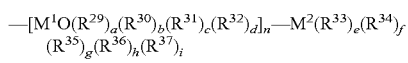

where p is 0 or 1; m is an integer of 1 to 3; $R^{11}$ is —CONH—; $R^{12}$ is a di-, tri- or tetra-valent hydrocarbon group having 1 to 39 carbon atoms where a part or the whole of hydrogen atoms may be replaced by fluorine atoms or a di-, tri- or tetra-valent hydrocarbon group having 1 to 99 carbon atoms and ether bond where a part or the whole of hydrogen atoms may be replaced by fluorine atoms; $Y^{1a}$ is a functional group represented by the formula:

—[$M^1O(R^{29})_a(R^{30})_b(R^{31})_c(R^{32})_d]_n$—$M^2(R^{33})_e(R^{34})_f$
($R^{35})_g(R^{36})_h(R^{37})_i$ where $M^1$ and $M^2$ are the same or different and each is a di-, tri-, tetra-, penta- or hexa-valent metal atom; a, b, c and d are 0 or 1, and a+b+c+d+2 is equal to the number of valences of the metal atom $M^1$; e, f, g, h and i are 0 or 1, and e+f+g+h+i+1 is equal to the number of valences of the metal atom $M^2$; $R^{29}$, $R^{30}$, $R^{31}$, $R^{32}$, $R^{33}$, $R^{34}$, $R^{35}$, $R^{36}$ and $R^{37}$ are the same or different and each is an organic group represented by the formula $OR^{38}$ or $R^{38}$ where $R^{38}$ is hydrogen atom or a hydrocarbon group having 1 to 10 carbon atoms in which a part or the whole of hydrogen atoms may be replaced by fluorine atoms, and at least one of $R^{29}$, $R^{30}$, $R^{31}$, $R^{32}$, $R^{33}$, $R^{34}$, $R^{35}$, $R^{36}$ and $R^{37}$ is $OR^{38}$; n is 0 or an integer of 1 to 11.

In the second polymer, it is preferable that the structural unit (A1) is a structural unit represented by the formula (A1-1):

(A1-1)

where $Rf^4$ and $Z^1$ are as defined in the formula (A1), or a structural unit represented by the formula (A1-2):

(A1-2)

where $Rf^4$ and $Z^1$ are as defined in the formula (A1), or the structural unit (A2) is a structural unit derived from at least one monomer selected from the group consisting of tetrafluoroethylene, vinylidene fluoride, chlorotrifluoroethylene and hexafluoropropylene.

The present invention also relates to a curable fluorine-containing resin composition comprising:

(a) the above-described first or second curable fluorine-containing polymer having a hydrolyzable metal alkoxide moiety, and (b) a curing agent.

Further the present invention relates to a curable fluorine-containing resin composition for coating comprising:

(a) the above-described first or second curable fluorine-containing polymer having a hydrolyzable metal alkoxide moiety, (b) a curing agent, and (c) a solvent.

By curing those curable compositions, a cured article and cured film having excellent characteristics can be provided.

The fluorine-containing compound which has a hydrolyzable metal alkoxide moiety, provides the structural unit M of the first and second polymers and is represented by the formula (1):

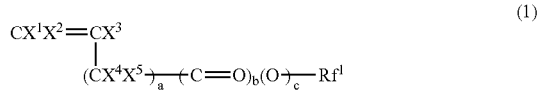
(1)

in which $X^1$ and $X^2$ are the same or different, and each is H or F; $X^3$ is H, F, $CH_3$ or $CF_3$; $X^4$ and $X^5$ are the same or different, and each is H, F or $CF_3$; $Rf^1$ is a fluorine-containing alkyl group having 1 to 40 carbon atoms or a fluorine-containing alkyl group having 2 to 100 carbon atoms and ether bond, which is an organic group in which 1 to 3 hydrogen atoms are replaced by $Y^1$ where $Y^1$ is a functional group containing, at its end, at least one hydrolyzable metal alkoxide moiety and having 1 to 50 carbon atoms; a is 0 or an integer of 1 to 3; b and c are the same or different, and each is 0 or 1, is a novel compound.

BEST MODE FOR CARRYING OUT THE INVENTION

Figure 1:
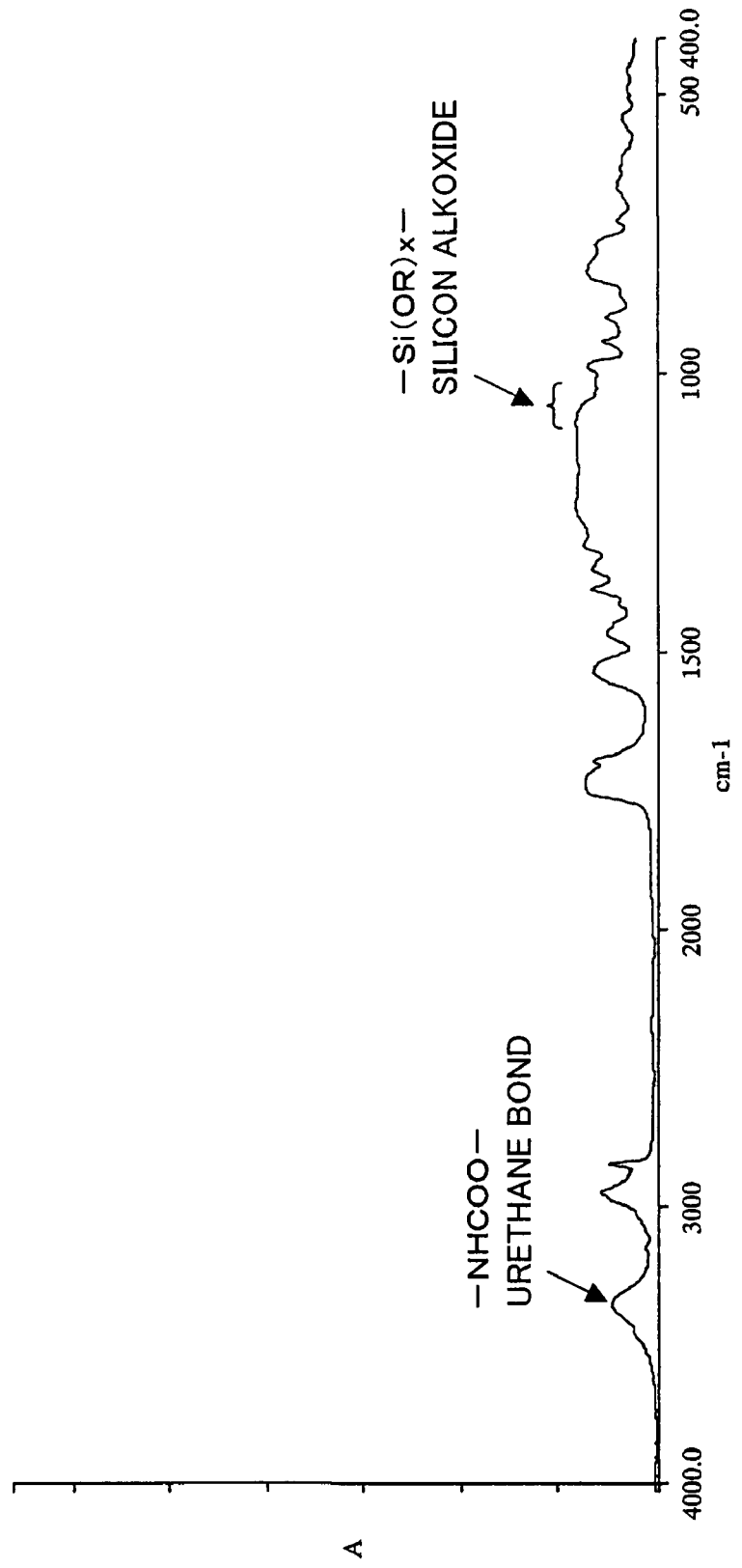
[FIG. 1] An IR chart of a fluorine-containing allyl ether monomer having a silicon alkoxide and synthesized in Example 1.

The first polymer of the present invention is the curable fluorine-containing polymer having a hydrolyzable metal alkoxide moiety which has a number average molecular weight of from 500 to 1,000,000 and is represented by the formula (2):

(2)

wherein the structural unit M is a structural unit having a hydrolyzable metal alkoxide moiety, the structural unit N is a structural unit having an ethylenic carbon-carbon double bond and the structural unit A is an optional structural unit, and the structural units M, N and A are contained in amounts of from 0.1 to 100% by mole, from 0 to 99.9% by mole and from 0 to 99.9% by mole, respectively.

Then each structural unit is explained below.

The structural unit M is the structural unit which is derived from a fluorine-containing ethylenic monomer having a hydrolyzable metal alkoxide moiety and is represented by the formula (M):

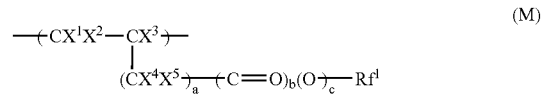
(M)

in which $X^1$ and $X^2$ are the same or different, and each is H or F; $X^3$ is H, F, $CH_3$ or $CF_3$; $X^4$ and $X^5$ are the same or different, and each is H, F or $CF_3$; $Rf^1$ is a fluorine-containing alkyl group having 1 to 40 carbon atoms or a fluorine-containing alkyl group having 2 to 100 carbon atoms and ether bond, which is an organic group in which 1 to 3 hydrogen atoms are replaced by $Y^1$ where $Y^1$ is a functional group containing, at its end, at least one hydrolyzable metal alkoxide moiety and having 1 to 50 carbon atoms; a is 0 or an integer of 1 to 3; b and c are the same or different, and each is 0 or 1.

The structural unit M is particularly preferably the structural unit M1 derived from a fluorine-containing ethylenic monomer and represented by the formula (M1):

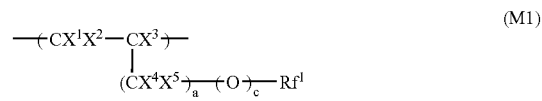
(M1)

wherein $X^1$, $X^2$, $X^3$, $X^4$, $X^5$, $Rf^1$, a and c are as defined above.

The fluorine-containing polymer having this structural unit M1 is preferable because particularly a refractive index is low, adhesion to various substrates such as a light scattering layer is good and durability can be enhanced.

Further one of more preferable examples of the structural unit M1 is the structural unit M2 derived from a fluorine-containing ethylenic monomer and represented by the formula (M2):

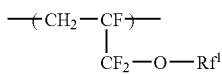
(M2)

wherein $Rf^1$ is as defined above.

This structural unit M2 is preferable because a refractive index is low, adhesion to various substrates such as a light scattering layer is good, durability can be enhanced, and in addition, copolymerizability with other fluorine-containing ethylenic monomers is good.

Also other preferable example of the structural unit M1 is the structural unit M3 derived from a fluorine-containing ethylenic monomer and represented by the formula (M3):

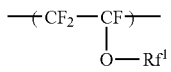
(M3)

wherein $Rf^1$ is as defined above.

This structural unit M3 is preferable because a refractive index is low, adhesion to various substrates such as a light scattering layer is good, durability can be enhanced, and in addition, copolymerizability with other fluorine-containing ethylenic monomers is good.

In the present invention, $Rf^1$ contained in the structural units M, M1, M2 and M3 is, as described above, an organic group having 1 to 3 functional groups $Y^1$ which contains, at its end, at least one hydrolyzable metal alkoxide moiety and has 1 to 50 carbon atoms, and an upper limit of the number of carbon atoms is preferably 30, more preferably 20, particularly preferably 10.

The hydrolyzable metal alkoxide moiety in the $Y^1$ functions to cause a hydrolysis and polycondensation reaction, thereby exhibiting an effect of enhancing good adhesion durability with a substrate having hydroxyl group.

It is preferable that $Rf^1$ is one represented by the formula (Rf1):

—D—Ry   (Rf1)

wherein —D— is a fluoroether unit represented by the formula (D):

(D)

in which n is an integer of 1 to 20; R is at least one selected from fluorine-containing divalent alkylene groups having 1 to 5 carbon atoms where at least one of hydrogen atoms is replaced by fluorine atom, and R may be the same or different when n is not less than two; Ry is a hydrocarbon group having 1 to 39 carbon atoms where a part or the whole of hydrogen atoms may be replaced by fluorine atoms or a hydrocarbon group having 1 to 99 carbon atoms and ether bond where a part or the whole of hydrogen atoms may be replaced by fluorine atoms, which is an organic group in which 1 to 3 hydrogen atoms are replaced by $Y^1$ ($Y^1$ is as defined above).

—R— is a fluorine-containing divalent alkylene group having 1 to 5 carbon atoms and has at least one fluorine atom, thereby being capable of contributing to further lowering of a viscosity of the compound, enhancement of heat resistance, lowering of a refractive index and enhancement of solubility in general purpose solvents as compared with conventional compounds having an alkylene ether unit or an alkoxyl group having no fluorine atom.

Examples of —(O—R)— or —(R—O)— in —D— are —(OCF$_2$CF$_2$CF$_2$)—, —(CF$_2$CF$_2$CF$_2$O)—, —(OCFQ$^1$CF$_2$)—, —(OCF$_2$CFQ$^1$)—, —(OCFQ$^2$)—, —(CFQ$^2$O)—, —(OCH$_2$CF$_2$CF$_2$)—, (OCF$_2$CF$_2$CH$_2$)—, —(OCH$_2$CH$_2$CF$_2$)—, —(OCF$_2$CH$_2$CH$_2$)—, —(OCF$_2$CF$_2$CF$_2$CF$_2$)—, —(CF$_2$CF$_2$CF$_2$CF$_2$O)—, —(OCFQ$^2$CH$_2$)—, —(CH$_2$CFQ$^2$O)—, —(OCH(CH$_3$)CF$_2$CF$_2$)—, —(OCF$_2$CF$_2$CH(CH$_3$))—, —(OCQ$^3$$_2$)—, —(CQ$^3$$_2$O)—, and the like, where Q$^1$ and Q$^2$ are the same or different and each is H, F or CF$_3$; Q$^3$ is CF$_3$. It is preferable that —D— is a repeating unit comprising one kind or two or more kinds thereof.

Specifically it is preferable that —D— is a repeating unit comprising one kind or two or more kinds selected from —(OCFQ$^1$CF$_2$)—, —(OCF$_2$CF$_2$CF$_2$)—, —(OCH$_2$CF$_2$CF$_2$)—, —(OCFQ$^2$)—, —(OCQ$^3$$_2$)—, —(CFQ$^1$CF$_2$O)—, —(CF$_2$CF$_2$CF$_2$O)—, —(CH$_2$CF$_2$CF$_2$O)—, —(CFQ$^2$O)— and —(CQ$^3$$_2$O)—, particularly preferably a repeating unit comprising one kind or two or more kinds selected from —(OCFQ$^1$CF$_2$)—, —(OCF$_2$CF$_2$CF$_2$)—, —(OCH$_2$CF$_2$CF$_2$)—, —(CFQ$^1$CF$_2$O)—, —(CF$_2$CF$_2$CF$_2$O)— and —(CH$_2$CF$_2$CF$_2$O)—, further preferably a repeating unit comprising one kind or two or more kinds selected from —(OCFQ$^1$CF$_2$)—, —(OCF$_2$CF$_2$CF$_2$)—, —(CFQ$^1$CF$_2$O)— and —(CF$_2$CF$_2$CF$_2$O)—.

It is to be noted that the —O—O— structural unit (specifically —R—O—O—R—, —O—O—R—, —R—O—O— or the like) is not contained in the above described fluorine-containing ether unit —D— and the above described $Rf^1$.

In the formula (Rf1), Ry is preferably a group represented by the formula (Ry):

—O—Ry$^1$   (Ry)

wherein Ry$^1$ is an organic-inorganic complex radical represented by the formula (Ry1):

—(R$^{11}$)$_p$R$^{12}$—(Y$^{1a}$)$_m$   (Ry1)

where p is 0 or 1; m is an integer of 1 to 3; R$^{11}$ is —CONH—; R$^{12}$ is a di-, tri- or tetra-valent hydrocarbon group having 1 to 39 carbon atoms where a part or the whole of hydrogen atoms may be replaced by fluorine atoms or a di-, tri- or tetra-valent hydrocarbon group having 1 to 99 carbon atoms and ether bond where a part or the whole of hydrogen atoms may be replaced by fluorine atoms; Y$^{1a}$ is a functional group represented by the formula:

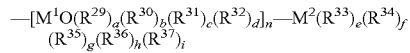

where M$^1$ and M$^2$ are the same or different and each is a di-, tri-, tetra-, penta- or hexa-valent metal atom; a, b, c and d are 0 or 1, and a+b+c+d+2 is equal to the number of valences of the metal atom M$^1$; e, f, g, h and i are 0 or 1, and e+f+g+h+i+1 is equal to the number of valences of the metal atom M$^2$; R$^{29}$, R$^{30}$, R$^{31}$, R$^{32}$, R$^{33}$, R$^{34}$, R$^{35}$, R$^{36}$ and R$^{37}$ are the same or different and each is an organic group represented by the formula: OR$^{38}$ or R$^{38}$ where R$^{38}$ is hydrogen atom or a hydrocarbon group having 1 to 10 carbon atoms in which a part or the whole of hydrogen atoms may be replaced by fluorine atoms, and at least one of $R^{29}$, $R^{30}$, $R^{31}$, $R^{32}$, $R^{33}$, $R^{34}$, $R^{35}$, $R^{36}$ and $R^{37}$ is $OR^{38}$; n is 0 or an integer of 1 to 11.

In the formula (Ry1), when p is 0, the end of Ry becomes an ether bond, and when p is 1, the end of Ry becomes a urethane bond.

Examples of —$R^{12}$— in the formula (Ry1) are, for instance, as follows.

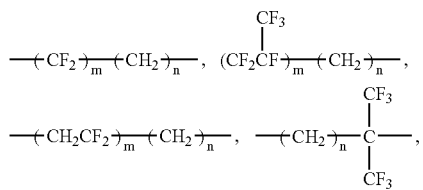

(in the above described groups, m: 0 to 10, n: 0 to 5, m+n: 1 to 15)

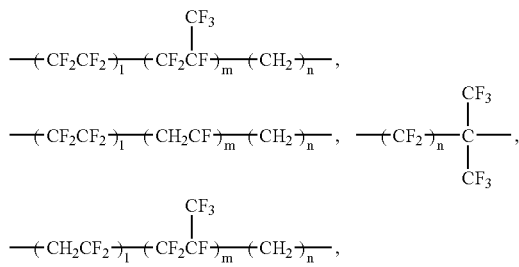

(in the above described groups, l: 1 to 10, m: 1 to 10, n: 0 to 5)

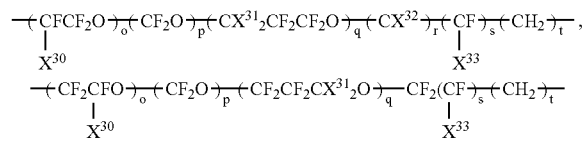
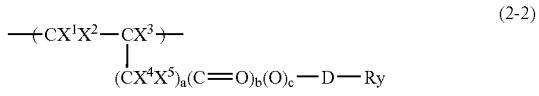

(in the above described groups, each of $X^{30}$ and $X^{33}$ is F or $CF_3$; each of $X^{31}$ and $X^{32}$ is H or F; o+p+q is 1 to 30; r is 0 or 1; s and t are 0 or 1)

and the like.

Examples of the metals $M^1$ and $M^2$ in $Y^{1a}$ are Cu as the IB group; Ca, Sr and Ba as the IIA group; Zn as the IIB group; B, Al and Ga as the IIIA group; Y as the IIIB group; Si and Ge as the IVA group; Pb as the IVB group; P and Sb as the VA group; V and Ta as the VB group; W as the VIB group; and La and Nd as the lanthanide.

Specifically metals of the IVA group, especially Si are preferable as $Y^{1a}$, and especially —$Si(OCH_3)_3$, —$Si(OC_2H_5)_3$, —$SiCH_3(OC_2H_5)_2$ and the like are preferable from the viewpoint of good adhesion to a substrate having hydroxyl group and durability after hydrolysis and polycondensation, and also —$[SiO(OCH_3)_2]_n$—$Si(OCH_3)_3$, —$[SiO(OC_2H_5)_2]_n$—$Si(OC_2H_5)_3$ and the like, where n is an integer of 1 to 11, are preferable from the viewpoint of enhancement of surface hardness in addition to good adhesion to a substrate having hydroxyl group and durability thereof after hydrolysis and polycondensation.

Of the above described groups, —$Si(OCH_3)_3$, —$Si(OC_2H_5)_3$, —$SiCH_3(OC_2H_5)_2$ and the like are particularly preferable as $Y^{1a}$.

With respect to the metals other than the IVA group, examples of $Y^{1a}$ are:

Ca of the IIA group: —$Ca(OR^{39})$, and a suitable example is —$Ca(OCH_3)$;

Zn of the IIB group: —$Zn(OR^{39})$, and a suitable example is —$Zn(OC_2H_5)$;

B of the IIIA group: —$B(OR^{39})_2$, and a suitable example is —$B(OCH_3)_2$;

Y of the IIIB group: —$Y(OR^{39})_2$, and a suitable example is —$Y(OC_4H_9)_2$;

Pb of the IVB group: —$Pb(OR^{39})_3$, and a suitable example is —$Pb(OC_4H_9)_3$;

Ta of the VB group: —$Ta(OR^{39})_4$, and a suitable example is —$Ta(OC_3H_7)_4$;

W of the VIB group: —$W(OR^{39})_5$, and a suitable example is —$W(OC_2H_5)_5$;

La of the lanthanide: —$La(OR^{39})_2$, and a suitable example is —$La(OC_3H_7)_2$;

and the like, wherein $R^{39}$ is a hydrocarbon group having 1 to 10 carbon atoms in which a part or the whole of hydrogen atoms may be replaced by fluorine atoms.

These various metals may be used in a combination of not only metals of the same kind but also metals of different kinds.

The structural unit M is preferably the structural unit M1, and the structural unit M1 is preferably the structural unit M2 or the structural unit M3. When —$Rf^1$ is represented by —D—Ry, the structural unit M is preferably the structural unit represented by the formula (2-2):

$$-\!\!+\!CX^1X^2-CX^3\!\!+\!- \qquad (2\text{-}2)$$
$$\quad\quad\quad\quad |$$
$$\quad\quad\quad (CX^4X^5)_a(C\!\!=\!\!O)_b(O)_c\!-\!D\!-\!Ry$$

wherein $X^1$, $X^2$, $X^3$, $X^4$, $X^5$, D, Ry, a, b and c are as defined above, from the viewpoint of decreasing a refractive index and a viscosity and also from the viewpoint of excellent adhesion durability to a substrate having hydroxyl group and heat resistance.

Specific examples of the structural unit M1 of the formula (2-2) are:

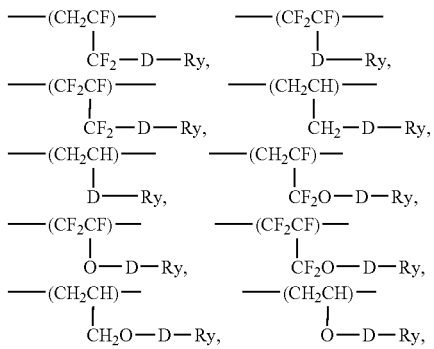

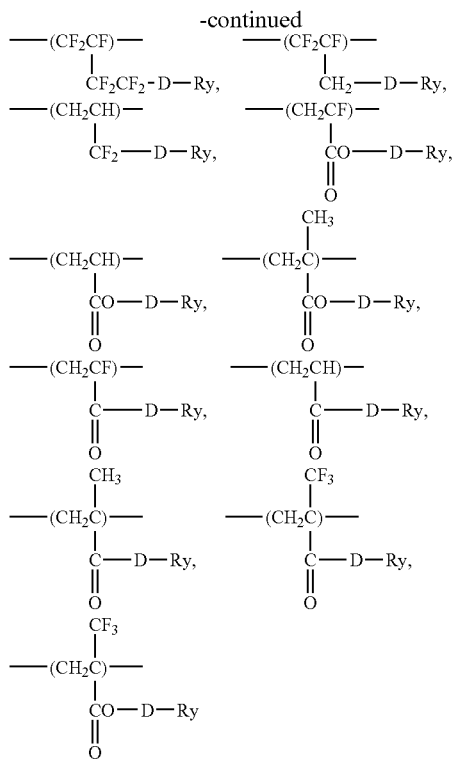

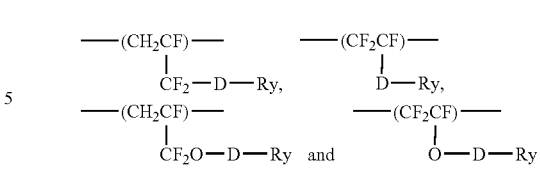

from the viewpoint of heat resistance and chemical resistance.

The structural unit N is an optional structural unit which is derived from a fluorine-containing ethylenic monomer and is represented by the formula (N):

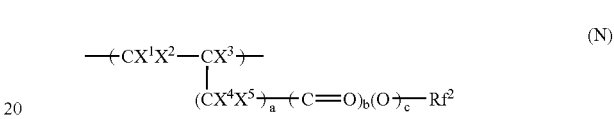

wherein $X^1$ and $X^2$ are the same or different, and each is H or F; $X^3$ is H, F, $CH_3$ or $CF_3$; $X^4$ and $X^5$ are the same or different, and each is H, F or $CF_3$; $Rf^2$ is a fluorine-containing alkyl group having 1 to 40 carbon atoms or a fluorine-containing alkyl group having 2 to 100 carbon atoms and ether bond, which is an organic group in which 1 to 3 hydrogen atoms are replaced by $Y^2$ where $Y^2$ is a monovalent organic group having 2 to 10 carbon atoms and containing, at its end, an ethylenic carbon-carbon double bond; a is 0 or an integer of 1 to 3; b and c are the same or different, and each is 0 or 1.

It is particularly preferable that the structural unit N is a structural unit N1 derived from a fluorine-containing ethylenic monomer and represented by the formula (N1):

and the like, and from the viewpoint of excellent heat resistance and chemical resistance, it is particularly preferable that the structural unit of the formula (2-2) is a structural unit represented by the formula (2-3):

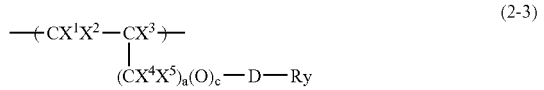

wherein $X^1$, $X^2$, $X^3$, $X^4$, $X^5$, D, Ry, a and c are as defined above.

More specific examples of the structural unit of the formula (2-3) are preferably:

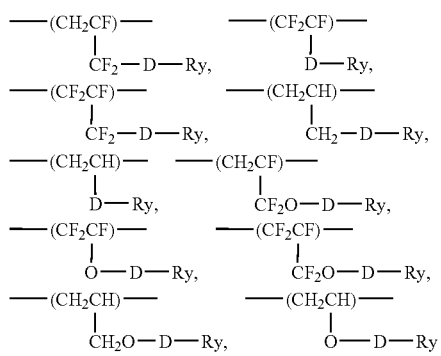

and the like, and particularly preferable are the structural units such as:

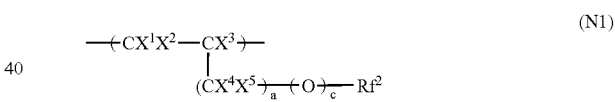

wherein $X^1$, $X^2$, $X^3$, $X^4$, $X^5$, $Rf^2$, a and c are as defined above.

The fluorine-containing polymer having this structural unit N1 is preferable because a curing reactivity by contact with a radical or a cation can be enhanced.

Further one of more preferable examples of the structural unit N1 is a structural unit N2 derived from a fluorine-containing ethylenic monomer and represented by the formula (N2):

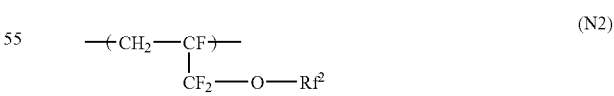

wherein $Rf^2$ is as defined above.

This structural unit N2 is a structural unit of a fluorine-containing allyl ether having an ethylenic carbon-carbon double bond at its end, and is preferable because not only near infrared transparency can be enhanced but also a refractive index can be decreased, and also polymerizability is good and copolymerizability with other fluorine-containing ethylenic monomers is satisfactory.

An another preferable example of the structural unit N1 is a structural unit N3 derived from a fluorine-containing ethylenic monomer and represented by the formula (N3):

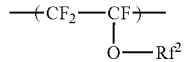
(N3)

wherein $Rf^2$ is as defined above.

This structural unit N3 is a structural unit of a fluorine-containing vinyl ether having an ethylenic carbon-carbon double bond at its end, and is preferable because not only near infrared transparency can be enhanced but also a refractive index can be decreased, and also copolymerizability with other fluorine-containing ethylenic monomers is satisfactory.

The $Y^2$ contained in the structural units N, N1, N2 and N3 is, as described supra, a monovalent organic group having 2 to 10 carbon atoms and containing an ethylenic carbon-carbon double bond at its end.

This carbon-carbon double bond contained in the $Y^2$ has an ability of causing a polycondensation reaction, and can provide a cured (crosslinked) article. Specifically a polymerization reaction or a condensation reaction is caused between the fluorine-containing polymer molecules or between the fluorine-containing polymer and the curing (crosslinking) agent to be added as case demands, for example, by a contact with a radical or a cation, and thereby a cured (crosslinked) article can be provided.

The first preferable $Y^2$ is:

wherein $Y^{2a}$ is an alkenyl group or fluorine-containing alkenyl group having 2 to 5 carbon atoms and containing an ethylenic carbon-carbon double bond at its end; d and e are the same or different and each is 0 or 1.

A preferable example of $Y^{2a}$ is:

—$CX^6$=$CX^7X^8$ wherein $X^6$ is H, F, $CH_3$ or $CF_3$; $X^7$ and $X^8$ are the same or different and each is H or F, and this group is preferable because a curing reactivity by a contact with a radical or a cation is high.

Preferable examples of $Y^{2a}$ are:

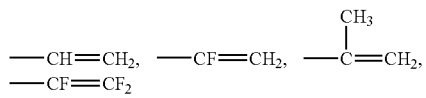

and the like.

A more preferable example of $Y^2$ is:

—O(C=O)$CX^6$=$CX^7X^8$ wherein $X^6$ is H, F, $CH_3$ or $CF_3$; $X^7$ and $X^8$ are the same or different and each is H or F, and this group is preferable because a curing reactivity by a contact with a radical is high and a cured article can be obtained easily by photo-curing.

Examples of the more preferable $Y^2$ described above are:

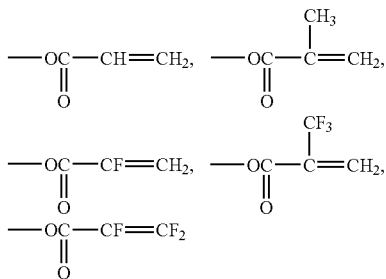

and the like.

Examples of other preferable $Y^2$ are:

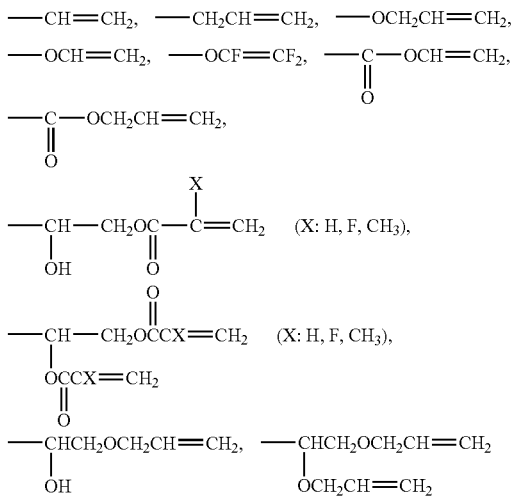

and the like.

Of the groups $Y^2$, those having a structure of —O(C=O)CF=$CH_2$ are preferable because near infrared transparency can be enhanced, a curing (crosslinking) reactivity is especially high and a cured article can be obtained efficiently.

The above described organic group $Y^2$ having a carbon-carbon double bond in its side chain may be introduced into the end of the polymer trunk chain.

In the fluorine-containing polymer used in the present invention, —$Rf^2$— (a group obtained by removing $Y^2$ from the mentioned —$Rf^2$) contained in the structural units N, N1, N2 and N3 is a fluorine-containing alkylene group having 1 to 40 carbon atoms or a fluorine-containing alkylene group having 2 to 100 carbon atoms and ether bond. In this $Rf^2$ group, a fluorine atom is to be bonded to the carbon atom contained therein, and is generally a fluorine-containing alkylene group or a fluorine-containing alkylene group having ether bond, in which a fluorine atom and hydrogen atom or a chlorine atom are bonded to the carbon atom. Preferable is the $Rf^2$ containing more fluorine atoms (a high fluorine content), and more preferable is a perfluoroalkylene group or a perfluoroalkylene group having ether bond. The fluorine content of the fluorine-containing polymer is not less than 25% by mass, preferably not less than 40% by mass. This fluorine content is preferable because not only a near infrared transparency of the fluorine-containing polymer can be enhanced but also a refractive index thereof can be decreased, and even if a curing degree (crosslinking density) is increased particularly for the purpose of enhancing heat resistance and elastic modulus of a cured article, a near infrared transparency can be maintained high or a refractive index can be maintained low.

When the number of carbon atoms of the —$Rf^2$— group is too large, in the case of fluorine-containing alkylene groups, in some cases, solubility in a solvent is lowered and transparency is lowered, and in the case of fluorine-containing alkylene groups having ether bond, in some cases, a hardness and mechanical characteristics of the polymer itself and the cured article obtained therefrom are lowered. Therefore too large number of carbon atoms is not preferable. The number of carbon atoms of fluorine-containing alkylene groups is preferably 1 to 20, more preferably 1 to 10, and the number of carbon atoms of fluorine-containing alkylene groups having ether bond is preferably 2 to 30, more preferably 2 to 20.

Preferable examples of —$Rf^2$— are:

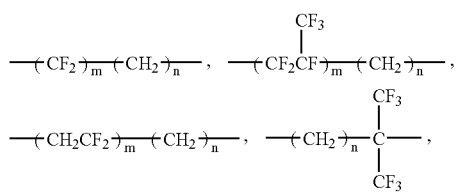

(In the above described groups, m: 0 to 10, n: 0 to 5)

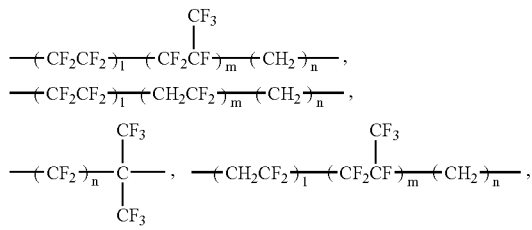

(In the above described groups, l: 1 to 10, m: 1 to 10, n: 0 to 5)

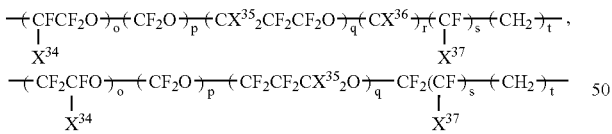

(In the above described groups, each of $X^{34}$ and $X^{37}$ is F or $CF_3$; each of $X^{35}$ and $X^{36}$ is H or F; o+p+q is 1 to 30; r is 0 or 1; s and t are 0 or 1), and the like.

As described above, the structural unit N constituting the fluorine-containing polymer used in the present invention is preferably the structural unit N1, and further the structural unit N1 is preferably the structural unit N2 or the structural unit N3. Then examples of the structural unit N2 and the structural unit N3 are explained below.

Preferable examples of the monomers constituting the structural unit N2 are:

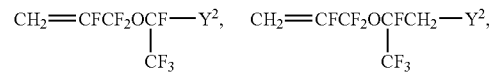

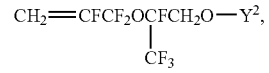

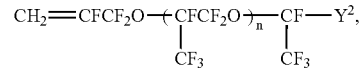

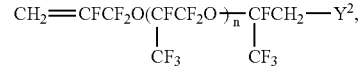

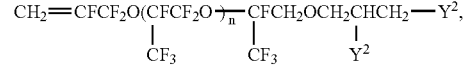

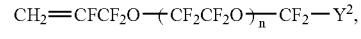

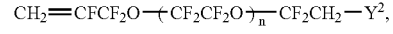

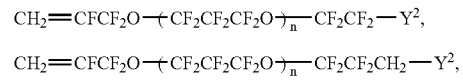

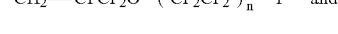

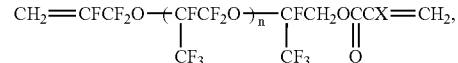

wherein n is an integer of 1 to 30; $Y^2$ is as defined above.

More specific examples thereof are:

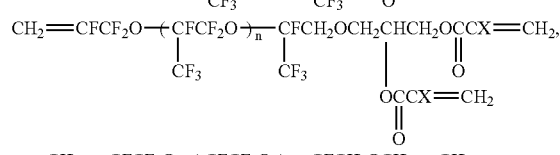

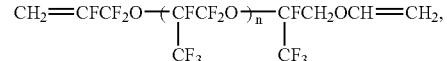

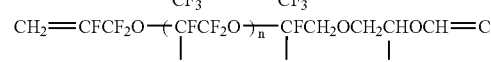

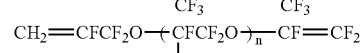

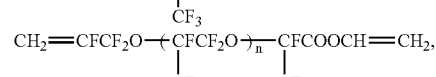

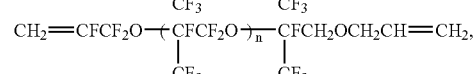

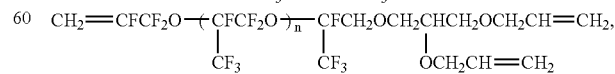

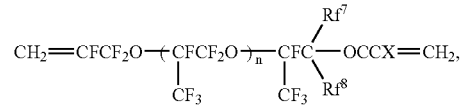

-continued

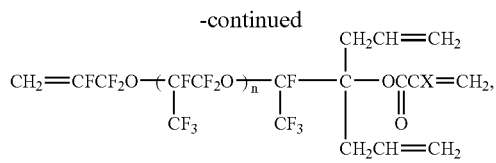

and the like, wherein $Rf^7$ and $Rf^8$ are perfluoroalkyl groups having 1 to 5 carbon atoms; n is 0 or an integer of 1 to 30; X is H, $CH_3$, F or $CF_3$.

Preferable examples of the monomers constituting the structural unit N3 are:

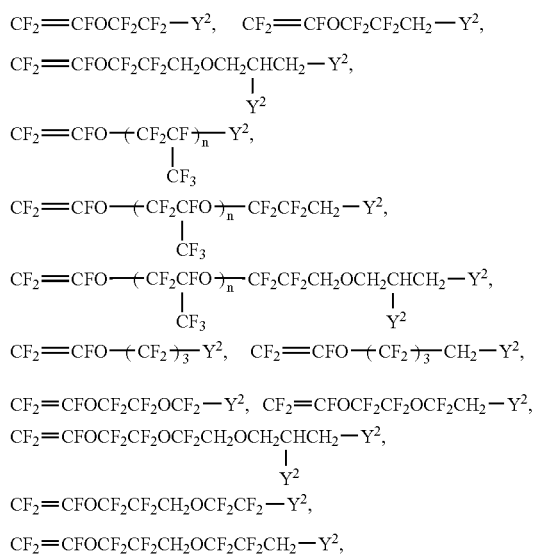

and the like, wherein $Y^2$ is as defined above; n is an integer of 1 to 30.

More specific examples thereof are:

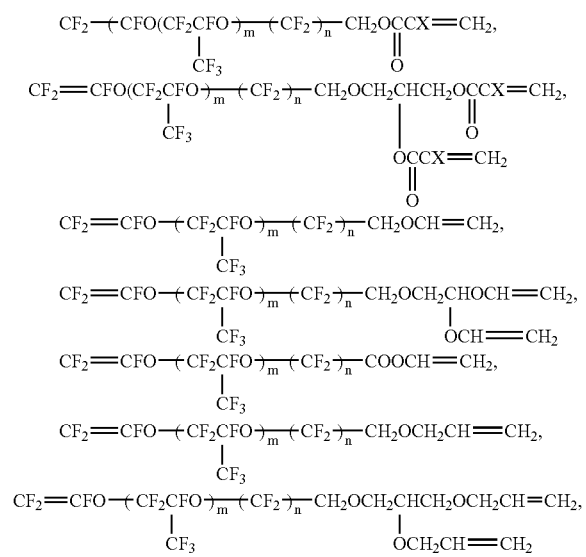

-continued

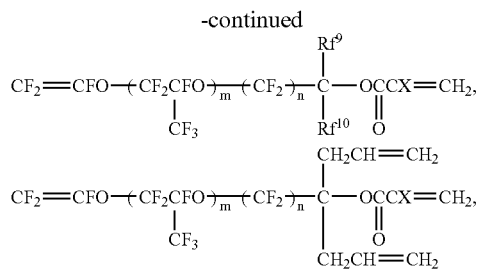

and the like, wherein $Rf^9$ and $Rf^{10}$ are perfluoroalkyl groups having 1 to 5 carbon atoms; m is 0 or an integer of 1 to 30; n is an integer of 1 to 3; X is H, $CH_3$, F or $CF_3$.

Preferable examples of monomers constituting the structural unit N of the fluorine-containing polymer other than the structural unit N2 and N3 are, for instance,

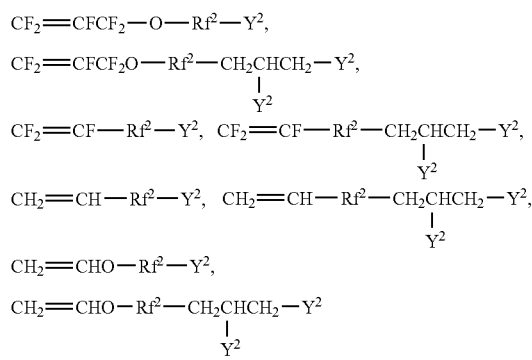

and the like, wherein $Y^2$ and $Rf^2$ are as exemplified above.

More specific examples thereof are:

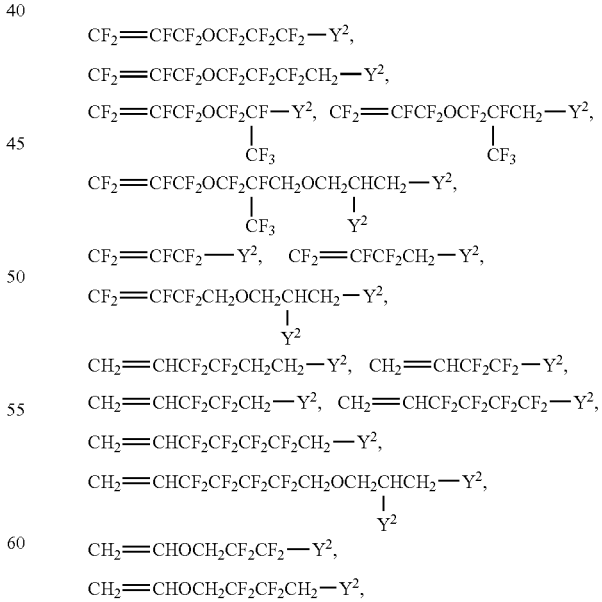

and the like, wherein $Y^2$ is as defined above.

The structural unit A is a structural unit derived from a monomer copolymerizable with the fluorine-containing ethylenic monomers providing the structural units represented by the formulae (M) and (N). The structural unit A is an optional component and is not limited as long as it is a monomer copolymerizable with the structural units M and N. The structural unit A may be optionally selected depending on intended applications of the fluorine-containing polymer and the cured article obtained therefrom and required characteristics.

Examples of the structural unit A are, for instance, the following structural units.

(A1) Structural Units Derived from Fluorine-Containing Ethylenic Monomers Having Functional Group These structural units (A1) are preferable because adhesion of the fluorine-containing polymer and the cured article thereof to a substrate and solubility in a solvent, particularly in general purpose solvents can be imparted and also because functions such as crosslinkability can be imparted.

Preferred structural units A1 of the fluorine-containing ethylenic monomer having functional group are structural units represented by the formula (A1):

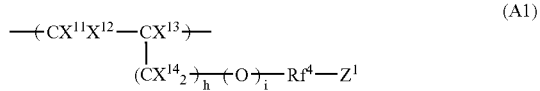

wherein $X^{11}$, $X^{12}$ and $X^{13}$ are the same or different and each is H or F; $X^{14}$ is H, F or $CF_3$; h is 0 or an integer of 1 or 2; i is 0 or 1; $Rf^4$ is a fluorine-containing divalent alkylene group having 1 to 40 carbon atoms or a fluorine-containing divalent alkylene group having 2 to 100 carbon atoms and ether bond; $Z^1$ is a functional group selected from the group consisting of —OH, $CH_2OH$, —COOH, a carboxylic acid derivative, —$SO_3H$, a sulfonic acid derivative, an epoxy group and a cyano group, and particularly preferred are structural units which are derived from:

wherein $Rf^4$ and $Z^1$ are as defined above, and are represented by the formula (A1-1):

wherein $Rf^4$ and $Z^1$ are as defined in the formula (A1).

Specific examples thereof are preferably structural units derived from fluorine-containing ethylenic monomers such as:

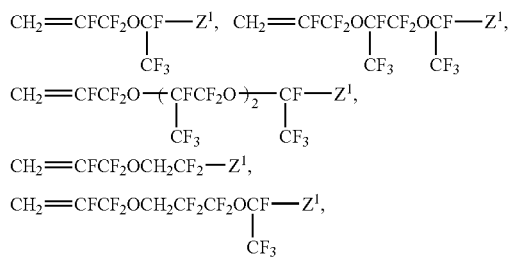

-continued

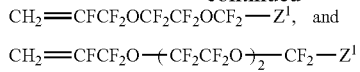

wherein $Z^1$ is as defined above.

Also there is preferably exemplified a structural unit which is derived from:

wherein $Rf^4$ and $Z^1$ are as defined above, and is represented by the formula (A1-2):

where $Rf^4$ and $Z^1$ are as defined in the formula (A1).

Specific examples thereof are structural units derived from monomers such as:

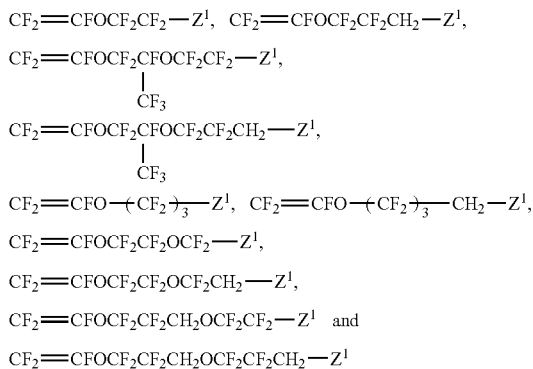

wherein $Z^1$ is as defined above.

Other examples of the fluorine-containing ethylenic monomer having functional group are:

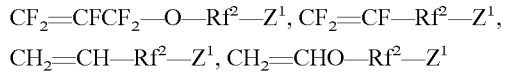

and the like, wherein —$Rf^2$— is the same as the above described —$Rf^2$— and $Z^1$ is as defined above. More specifically there are:

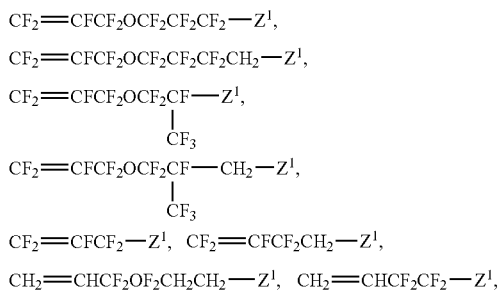

-continued

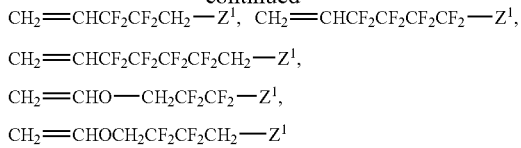

and the like, wherein $Z^1$ is as defined above.

(A2) Structural Units Derived from Fluorine-Containing Ethylenic Monomers Having no Functional Group These structural units A2 are preferable from the point that a refractive index of the fluorine-containing polymer and the cured article obtained therefrom can be maintained low and because a refractive index can be further decreased. Also these structural units are preferable from the point that by selecting the monomer, mechanical characteristics and glass transition temperature of the polymer can be adjusted, and particularly the glass transition temperature can be increased by copolymerization with the structural units M and N.

Examples of the preferred structural units (A2) of the fluorine-containing ethylenic monomer are those represented by the formula (A2):

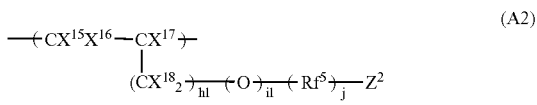

wherein $X^{15}$, $X^{16}$ and $X^{18}$ are the same or different and each is H or F; $X^{17}$ is H, F or $CF_3$; h1, i1 and j are the same or different and each is 0 or 1; $Z^2$ is H, F, Cl or a linear or branched perfluoroalkyl group having 1 to 16 carbon atoms; $Rf^5$ is a fluorine-containing divalent alkylene group having 1 to 20 carbon atoms or a fluorine-containing divalent alkylene group having 2 to 100 carbon atoms and ether bond.

Examples thereof are preferably structural units derived from monomers such as:

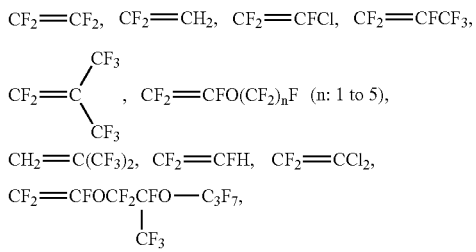

$CH_2\!\!=\!\!CF\text{-}(CF_2)_n\text{-}Z^2$ ($Z^2$ is as defined in the formula (A2), n is from 1 to 10) and $CH_2\!\!=\!\!CHOCH_2\text{-}(CF_2)_n\text{-}Z^2$ ($Z^2$ is as defined in the formula (A2), n is from 1 to 10).

It is particularly preferable that these structural units are structural units derived from at least one monomer selected from the group consisting of tetrafluoroethylene, vinylidene fluoride, chlorotrifluoroethylene and hexafluoropropylene because a refractive index of the curable fluorine-containing polymer and the cured article obtained therefrom can be maintained low.

(A3) Fluorine-Containing Aliphatic Ring Structural Units

Introduction of these structural units A3 is preferable since transparency can be increased, and also the fluorine-containing polymer having a high glass transition temperature can be obtained and a higher hardness of the cured article can be expected.

Examples of the preferred fluorine-containing aliphatic ring structural unit A3 are those represented by the formula (A3):

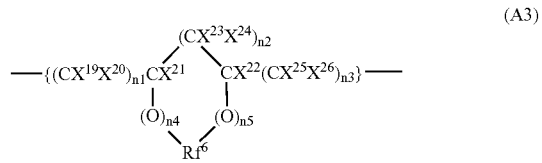

wherein $X^{19}$, $X^{20}$, $X^{23}$, $X^{24}$, $X^{25}$ and $X^{26}$ are the same or different and each is H or F; $X^{21}$ and $X^{22}$ are the same or different and each is H, F, Cl or $CF_3$; $Rf^6$ is a fluorine-containing alkylene group having 1 to 10 carbon atoms or a fluorine-containing alkylene group having 2 to 10 carbon atoms and ether bond; n2 is 0 or an integer of from 1 to 3; n1, n3, n4 and n5 are the same or different and each is 0 or 1.

For example, there are structural units represented by:

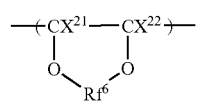

wherein $Rf^6$, $X^{21}$ and $X^{22}$ are as defined above.

Specifically there are:

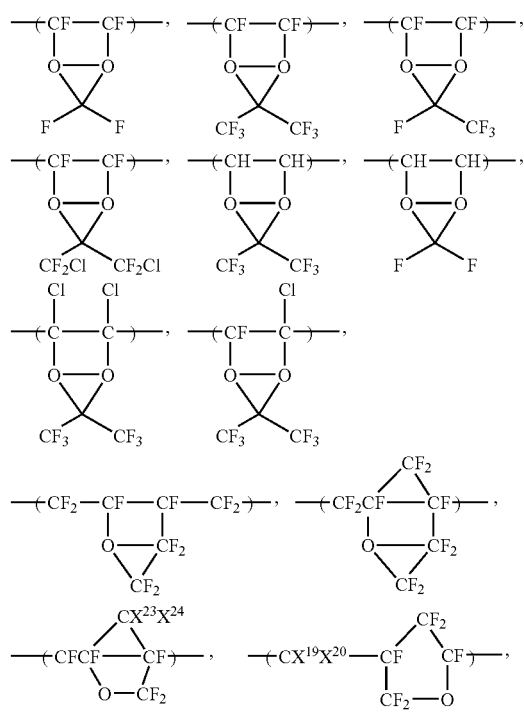

-continued

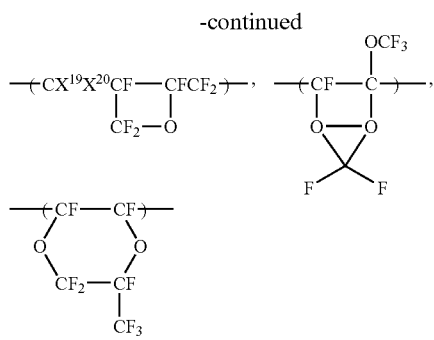

and the like wherein $X^{19}$, $X^{20}$, $X^{23}$ and $X^{24}$ are as defined above.

Other examples of the fluorine-containing aliphatic ring structural units are, for instance,

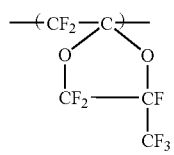

and the like.

(A4) Structural Units Derived from Ethylenic Monomers Having no Fluorine

The introduction of those structural units A4 can enhance solubility in general-purpose solvents and can improve compatibility with additives, for example, a photocatalyst and a curing agent to be added as case demands.

Examples of the non-fluorine-containing ethylenic monomer are as follows.

α-Olefins:
Ethylene, propylene, butene, vinyl chloride, vinylidene chloride and the like.

Vinyl Ether or Vinyl Ester Monomers:
$CH_2$=CHOR, $CH_2$=CHOCOR (R: hydrocarbon group having 1 to 20 carbon atoms) and the like.

Allyl Monomers:
$CH_2$=CHCH$_2$Cl, $CH_2$=CHCH$_2$OH, $CH_2$=CHCH$_2$COOH, $CH_2$=CHCH$_2$Br and the like.

Allyl Ether Monomers:
$CH_2$=CHCH$_2$OR
(R: hydrocarbon group having 1 to 20 carbon atoms),

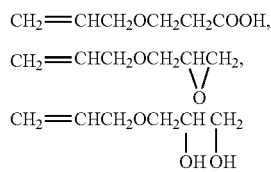

and the like.

Acrylic or Methacrylic Monomers:
Acrylic acid, methacrylic acid, acrylic esters, methacrylic acid esters, maleic anhydride, maleic acid, maleic acid esters and the like.

Monomers obtained by replacing a part or the whole of hydrogen atoms of those non-fluorine-containing ethylenic monomers with heavy hydrogen atoms are more preferred from the viewpoint of transparency.

(A5) Structural Units Derived from Alicyclic Monomers

The structural unit A5 of an alicyclic monomer may be introduced as a component copolymerizable with the structural units M and N, more preferably as the third component in addition to the structural units M and N and the structural unit of the above-mentioned fluorine-containing ethylenic monomer or non-fluorine-containing ethylenic monomer (the above-mentioned A3 or A4), thereby making a glass transition temperature and a hardness high.

Examples of the alicyclic monomer A5 are norbornene derivatives represented by:

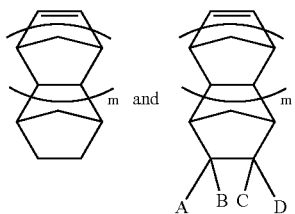

wherein m is 0 or an integer of from 1 to 3; A, B, C and D are the same or different and each is H, F, Cl, COOH, $CH_2OH$, a perfluoroalkyl group having 1 to 5 carbon atoms or the like, alicyclic monomers such as:

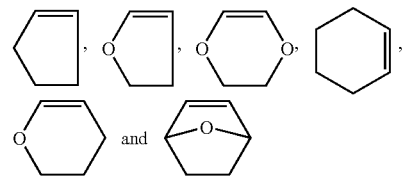

and derivatives thereof to which a substituent is introduced.

The first fluorine-containing polymer may be a homopolymer of the structural unit M or may be a copolymer of the structural unit M with the structural unit N and further the structural unit A.

The homopolymer is advantageous from the point that a refractive index can be maintained low, functions of imparting a near infrared transparency and adhesion durability to a substrate having hydroxyl group can be imparted, and further a high hardness of a coating film can be obtained.

Also in the case of the copolymer, the content of the structural unit M may be not less than 0.1% by mole based on the whole structural units constituting the fluorine-containing polymer, and it is preferable that the content is not less than 2.0% by mole, preferably not less than 5% by mole, more preferably not less than 10% by mole in order to obtain a cured article having a high hardness by curing (crosslinking) and excellent abrasion resistance, scratch resistance, chemical resistance and solvent resistance.

Particularly in applications requiring formation of a cured coating film being excellent in heat resistance and transparency and low in water absorption, the content of the structural unit M is not less than 10% by mole, preferably not less than 20% by mole, further preferably not less than 30% by mole, particularly preferably not less than 40% by mole. An upper limit thereof is less than 100% by mole.

A molecular weight, for example, a number average molecular weight of the fluorine-containing polymer can be selected within a range from 500 to 1,000,000, preferably from 1,000 to 500,000, particularly from 2,000 to 200,000.

If the molecular weight is too low, mechanical properties tend to be insufficient even after the curing, and particularly a cured article and a cured coating film tend to be fragile and insufficient in strength. If the molecular weight is too high, solubility in a solvent is lowered, particularly film forming property and leveling property are apt to be lowered at forming a thin film and storage stability of the fluorine-containing polymer tends to be unstable. The number average molecular weight is most preferably selected within a range from 5,000 to 100,000.

The second polymer of the present invention is a curable fluorine-containing polymer having a hydrolyzable metal alkoxide moiety which has a number average molecular weight of from 500 to 1,000,000 and is represented by the formula (2-1):

(2-1)

wherein the structural unit M and the structural unit N are the same as in the first polymer and the structural unit A1 and the structural unit A2 are as defined above, the structural units M, N, A1 and A2 are contained in amounts of from 0.1 to 90% by mole, from 0 to 99.9% by mole, from 0 to 99.9% by mole and from 0 to 99.9% by mole, respectively, and N+A1+A2 is contained in an amount of from 10 to 99.9% by mole.

The content of the structural unit M in the second fluorine-containing polymer is not less than 0.1% by mole based on the whole structural units constituting the fluorine-containing polymer. In order to obtain a cured article having a high hardness by curing (crosslinking) and excellent abrasion resistance, scratch resistance, chemical resistance and solvent resistance, it is preferable that the content is not less than 2.0% by mole, preferably not less than 5% by mole, more preferably not less than 10% by mole. Particularly in applications requiring formation of a cured film having excellent heat resistance and transparency and low water absorption, it is preferable that the content is not less than 10% by mole, preferably not less than 20% by mole, more preferably not less than 50% by mole. An upper limit of the content is less than 100% by mole.

The contents of the structural units N, A1 and A2 are each not more than 99.9% by mole. The total percent by mole of N+A1+A2 is from 10 to 99.9% by mole. When the total percent by mole is less than 10% by mole, a refractive index cannot be maintained low, and further a hardness of the cured film after the curing tends to become low, which is not preferable. A more preferable total percent by mole of N+A1+A2 is not less than 20% by mole, further preferably not less than 30% by mole, and not more than 60% by mole, further preferably not more than 50% by mole.

From the viewpoint that a strength and abrasion resistance of a cured film after the curing can be enhanced, a molar ratio (N/(N+A1+A2)) of the structural unit N to the sum of the structural units N, A1 and A2 in the second fluorine-containing polymer is preferably 1/100 to 100/100, more preferably 30/100 to 100/100, further preferably 50/100 to 100/100, particularly preferably 70/100 to 100/100.

Further from the viewpoint that adhesion of a cured film to a substrate and durability thereof can be enhanced, a molar ratio (A1/(N+A1+A2)) of the structural unit A1 to the sum of the structural units N, A1 and A2 in the second fluorine-containing polymer is preferably 1/100 to 50/100, more preferably 1/100 to 40/100, further preferably 1/100 to 30/100.

A molecular weight, for example, a number average molecular weight of the second fluorine-containing polymer can be selected within a range from 500 to 1,000,000, preferably from 1,000 to 500,000, particularly preferably from 2,000 to 200,000.

If the molecular weight is too low, mechanical properties tend to be insufficient even after the curing, and particularly a cured article and a cured coating film tend to be fragile and insufficient in a strength. If the molecular weight is too high, solubility in a solvent is lowered, particularly film forming property and leveling property are apt to be lowered at forming a thin film, and storage stability of the fluorine-containing polymer tends to be lowered. The number average molecular weight is most preferably selected within a range from 5,000 to 100,000.

As mentioned above, it can be said that the second polymer comprises, as essential structural units, the structural unit N and/or the structural unit A which are optional structural units of the first polymer, and is specifically so defined.

In the second fluorine-containing polymer of the present invention, with respect to combinations and proportions of the structural unit M (M1, M2 and M3), the structural unit N(N1, N2 and N3), and further the structural unit A (A1 and A2), various combinations of the structural unit M, the structural unit N and the structural unit A can be selected from the above described examples, depending on intended applications, physical properties (particularly glass transition temperature, hardness, etc.), functions (transparency) and the like.

Also the fluorine-containing polymer is preferably soluble in general purpose solvents, for example, in at least one of ketone solvents, acetic acid ester solvents, alcohol solvents and aromatic solvents or in solvent mixtures containing at least one of general purpose solvents.

The fluorine-containing polymer being soluble in general purpose solvents is preferable because film forming property and homogeneity are excellent particularly in forming a thin film having a thickness of not more than 0.3 µm, for example, of the order of 0.1 µm in a process for forming a coating film, and also is advantageous from the viewpoint of productivity.

For obtaining the fluorine-containing polymer of the present invention, generally any of the following methods can be adopted.

(1) A method of previously synthesizing a monomer having $Rf^1$ and then polymerizing the monomer (2) A method of once synthesizing a polymer having another functional group and then converting the functional group through polymer reaction, thus introducing the functional group $Rf^1$ to the polymer (3) A method of introduction by both of the methods (1) and (2)

Of these methods, the method of (3) is preferable because the curable fluorine-containing polymer of the present invention having a hydrolyzable metal alkoxide moiety is obtained without a curing reaction of the carbon-carbon double bond at an end of a side chain of the fluorine-containing polymer.

For the polymerization, radical polymerization method, anionic polymerization method, cationic polymerization method and the like can be employed. Of these methods, the radical polymerization method is particularly preferable because in the case of the monomers exemplified for obtaining the polymer having a hydrolyzable metal alkoxide moiety, it is easy to control quality of the polymer such as a composition and a molecular weight and produce the polymer on an industrial scale.

The fluorine-containing ethylenic monomer providing the structural unit M, namely the fluorine-containing compound having a hydrolyzable metal alkoxide moiety and represented by the formula (1):

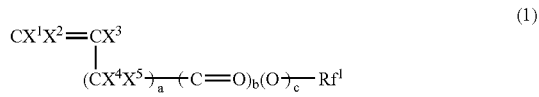

wherein $X^1$ and $X^2$ are the same or different, and each is H or F; $X^3$ is H, F, $CH_3$ or $CF_3$; $X^4$ and $X^5$ are the same or different, and each is H, F or $CF_3$; $Rf^1$ is a fluorine-containing alkyl group having 1 to 40 carbon atoms or a fluorine-containing alkyl group having 2 to 100 carbon atoms and ether bond, which is an organic group in which 1 to 3 hydrogen atoms are replaced by $Y^1$ where $Y^1$ is a functional group containing, at its end, at least one hydrolyzable metal alkoxide moiety and having 1 to 50 carbon atoms; a is 0 or an integer of 1 to 3; b and c are the same or different, and each is 0 or 1, is a novel compound.

A means of initiating the polymerization of such a novel fluorine-containing compound is not limited particularly as long as the polymerization proceeds radically. The polymerization is initiated, for example, with an organic or inorganic radical polymerization initiator, heat, light, ionizing radiation or the like. The polymerization can be carried out by solution polymerization, bulk polymerization, suspension polymerization, emulsion polymerization or the like.

In this novel fluorine-containing compound, the preferable examples of the structural unit M1, M2 and M3 explained supra and Ry and $Y^1$ explained specifically in $Rf^1$ are also used.

The present invention also relates to the curable fluorine-containing resin composition comprising:

(a) the first or second curable fluorine-containing polymer having a hydrolyzable metal alkoxide moiety, and (b) a curing agent.

As the curing agent (b), thermally curable or two-component cold curing agents in addition to active energy curing initiators can be used, and active energy curing initiators are preferable because the composition is applicable to, for example, transparent resin substrates since a curing reaction can be carried out at relatively low temperatures.

The active energy curing initiator is a compound which generates a radical or a cation (acid) only by irradiation of active energy rays such as electromagnetic wave having a wavelength of not more than 350 nm, namely ultraviolet ray, electron beam, X-ray or γ-ray, and functions as a catalyst for initiating the curing (crosslinking reaction) of the crosslinkable group (for example, carbon-carbon double bond) of the fluorine-containing prepolymer. Usually, initiators generating a radical or a cation (acid) by means of ultraviolet ray, particularly those generating a radical are used.

According to the curable fluorine-containing resin composition of the present invention, since a curing reaction can be initiated easily with the above described active energy rays, heating at high temperature is not necessary, and a curing reaction can be carried out at relatively low temperature. Therefore, the composition is preferable since it is applicable to substrates, for example, even transparent resin substrates which have low heat resistance and are easily subject to deformation, decomposition and coloration with heat.

The composition of the present invention is suitable particularly as a starting material for a laminated article which has anti-glaring property and low reflection and is used for suppressing lowering of visibility of an image in image displaying apparatuses such as a liquid crystal display (LCD), a flat panel display (FPD), an organic electroluminescent device (EL) and a plasma display (PDP).

The curing agent (b) in the composition of the present invention is optionally selected depending on kind of the crosslinkable group (for example, a hydrolyzable metal alkoxide moiety or a carbon-carbon double bond) in the fluorine-containing polymer (a) (whether the group is radically reactive or cationically (acid) reactive), kind of active energy rays (wavelength range) to be used, intensity of irradiation, and the like.

Generally examples of the initiator (photo-radical generator) for curing by using active energy rays in an ultraviolet region are, for instance, as follows.

Acetophenone Initiators

Acetophenone, chloroacetophenone, diethoxyacetophenone, hydroxyacetophenone, α-aminoacetophenone and the like.

Benzoin Initiators

Benzoin, benzoin methyl ether, benzoin ethyl ether, benzoin isopropyl ether, benzoin isobutyl ether, benzyldimethylketal and the like.

Benzophenone Initiators

Benzophenone, benzoylbenzoic acid, methyl o-benzoylbenzoate, 4-phenylbenzophenone, hydroxybenzophenone, hydroxy-propylbenzophenone, acrylated benzophenone, Michler's ketone and the like.

Thioxanthone Initiators

Thioxanthone, chlorothioxanthone, methylthioxanthone, diethylthioxanthone, dimethylthioxanthone and the like.

Other Initiators

Benzyl, α-acyloxime ester, acylphosphine oxide, glyoxyester, 3-ketocoumaran, 2-ethylanthraquinone, camphorquinone, anthraquinone and the like.

Also photo initiators such as amines, sulfones and sulfines may be added as case demands.

Also examples of cationically (acid) reactive initiators (photoacid generators) are as follows.

Onium Salts

Iodonium salt, sulfonium salt, phosphonium salt, diazonium salt, ammonium salt, pyridinium salt and the like.

Sulfone Compounds

β-keto ester, β-sulfonyl sulfone, α-diazo compounds thereof and the like.

Sulfonic Acid Esters

Alkyl sulfonate, haloalkyl sulfonate, aryl sulfonate, imino sulfonate and the like.

Others

Sulfonimide compounds, diazomethane compounds and the like.

In the curable fluorine-containing resin composition of the present invention, an adding amount of the curing initiator is optionally selected depending on the content of crosslinkable group in the fluorine-containing polymer (I), further kinds of the initiator and the active energy ray to be used, and an amount of irradiation energy (intensity and time). The amount of the curing initiator is from 0.01 to 30 parts by mass, further from 0.05 to 20 parts by mass, most preferably from 0.1 to 10 parts by mass based on 100 parts by mass of the fluorine-containing polymer (a).

To the curable fluorine-containing resin composition of the present invention may be blended various additives, as case demands, in addition to the above described compounds.

Examples of such additives are, for instance, a silane coupling agent, a plasticizer, a discoloration inhibitor, an antioxidant, an inorganic filler, a leveling agent, a viscosity regulating agent, a light stabilizer, a water absorbent, a pigment, a dye, a reinforcing agent and the like.

Also to the composition of the present invention can be blended fine particles or ultrafine particles of inorganic compounds for the purposes of increasing a hardness of a cured article and regulating a refractive index.

The fine particles of inorganic compound are not limited particularly, and preferred are compounds having a refractive index of not more than 1.5. Specifically desirable are fine particles of magnesium fluoride (refractive index: 1.38), silicon oxide (refractive index: 1.46), aluminum fluoride (refractive index: 1.33 to 1.39), calcium fluoride (refractive index: 1.44), lithium fluoride (refractive index: 1.36 to 1.37), sodium fluoride (refractive index: 1.32 to 1.34), thorium fluoride (refractive index: 1.45 to 1.50) and the like. It is desirable that a particle size of the fine particles is small enough as compared with a wavelength of visible light in order to secure transparency of the material having a low refractive index. Specifically the particle size is not more than 100 nm, particularly preferably not more than 50 nm.

In regulating the refractive index, it is possible to form a cavity with fine particles or ultrafine particles of the inorganic compound. Namely, in a coating film obtained using the composition of the present invention blended with fine particles or ultrafine particles of the inorganic compound, by use of this cavity, it is possible to make its refractive index lower as compared with a refractive index of a coating film produced using no fine particles of inorganic compound.

When using the fine particles of inorganic compound, it is desirable that the fine particles of inorganic compound are used in the form of organic sol in which the fine particles have been previously dispersed in an organic dispersant in order not to lower dispersion stability in the composition, adhesion in the low refractive index material and the like. Further surfaces of the fine particles of inorganic compound can be decorated previously with various coupling agents or the like in order to enhance dispersion stability, adhesion in the low refractive index material and the like of the fine particles of inorganic compound in the composition. Examples of the coupling agents are, for instance, organosilicon compounds; metal alkoxides such as aluminum, titanium, zirconium, antimony and a mixture thereof; salts of organic acid; coordination compounds having ligand; and the like.

In the fluorine-containing resin composition of the present invention for coating, the curable fluorine-containing polymer (a) or the additives may be in the form of dispersion or solution in the solvent (c). Being in the form of uniform solution is preferred to form a uniform thin coating film and also to enable the film to be formed at relatively low temperature.

The present invention also relates to the curable fluorine-containing resin composition for coating obtained by blending a solvent to the above-mentioned curable fluorine-containing resin composition The solvent to be used is not limited particularly as long as the fluorine-containing polymer (a), the curing agent, and additives to be added as case demands such as a leveling agent and a light stabilizer are uniformly dissolved or dispersed in it. Particularly preferred is a solvent dissolving the fluorine-containing polymer (a) uniformly.

Examples of the solvent are, for instance, cellosolve solvents such as methyl cellosolve, ethyl cellosolve, methyl cellosolve acetate and ethyl cellosolve acetate; ester solvents such as diethyl oxalate, ethyl pyruvate, ethyl-2-hydroxybutyrate, ethyl acetoacetate, butyl acetate, amyl acetate, ethyl butyrate, butyl butyrate, methyl lactate, ethyl lactate, methyl 3-methoxypropionate, ethyl 3-methoxypropionate, methyl 2-hydroxyisobutyrate and ethyl 2-hydroxyisobutyrate; propylene glycol solvents such as propylene glycol monomethyl ether, propylene glycol monoethyl ether, propylene glycol monobutyl ether, propylene glycol monomethyl ether acetate, propylene glycol monoethyl ether acetate, propylene glycol monobutyl ether acetate and dipropylene glycol dimethyl ether; ketone solvents such as 2-hexanone, cyclohexanone, methyl amino ketone and 2-heptanone; alcohol solvents such as methanol, ethanol, propanol, isopropanol and butanol; aromatic hydrocarbons such as toluene and xylene; solvent mixtures of two or more thereof and the like.

Also in order to enhance solubility of the fluorine-containing polymer (a), a fluorine-containing solvent may be used as case demands.

Examples of the fluorine-containing solvent are, for instance, $CH_3CCl_2F$ (HCFC-141b), a mixture of $CF_3CF_2CHCl_2$ and $CClF_2CF_2CHClF$ (HCFC-225), perfluorohexane, perfluoro(2-butyltetrahydrofuran), methoxy-nonafluorobutane, 1,3-bistrifluoromethylbenzene, and in addition, fluorine-containing alcohols such as:

$H(CF_2CF_2)_nCH_2OH$ (n: an integer of from 1 to 3),
$F(CF_2)_nCH_2OH$ (n: an integer of from 1 to 5) and
$CF_3CH(CF_3)OH$, benzotrifluoride, perfluorobenzene, perfluoro(tributylamine), $ClCF_2CFClCF_2CFCl_2$ and the like.

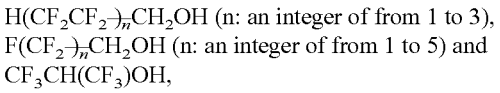

Those fluorine-containing solvents may be used solely, in a mixture thereof or in a mixture of one or more of the fluorine-containing solvents and non-fluorine-containing solvents.

Among them, ketone solvents, acetic acid ester solvents, alcohol solvents and aromatic solvents are preferred from the viewpoint of coatability and productivity in coating.

The solid content of the coating composition is good enough as far as coatability is good, a low molecular weight monomer component etc. hardly remain in the coating film after the curing and the surface of the coating film is free from tackiness. For example, the solid content may be selected within a range of the order of 0.5 to 10% by mass.

The curable fluorine-containing resin composition of the present invention is formed into a cured article or a cured film by curing, for example, by photocuring, and can be applied to various substrates and can be used to various applications.

Kind of a product, namely kind of a substrate which is provided with a low reflection by means of the cured article or the cured film is not limited particularly. Examples of the substrate are, for instance, inorganic materials such as glass, stone, concrete and tile; metals such as iron, aluminum and copper; wood, paper, printed matter, printing paper, picture and the like.

Further there are synthetic resins such as a vinyl chloride resin, polyethylene terephthalate, cellulose resin such as tri-acetyl cellulose, polycarbonate resin, polyolefin resin, acrylic resin, phenol resin, xylene resin, urea resin, melamine resin, diallyl phthalate resin, furan resin, amino resin, alkyd resin, urethane resin, vinyl ester resin, polyimide resin and polyamide resin.

When a certain portion of the product other than a specific portion thereof is provided with the laminated article and the shape of the specific portion is lifted up by a reflecting light, a decorative effect of the article can be enhanced.

Among the substrates, an anti-glaring substrate for liquid crystal display (LCD) has a surface coated with fine inorganic particles, and is used preferably and as a result, can effectively exhibit anti-glaring property and a low reflection effect.

The composition of the present invention is effectively applied on the following articles.

Optical parts such as prism, lens sheet, polarizing plate, optical filter, lenticular lens, Fresnel lens, screen of rear projection display, lens for reduction projection type exposure meter, optical fiber and optical coupler; transparent protection plates represented by glass for show window, glass for show case, a cover for advertisement and a cover for photo-stand; protection plates for CRT, liquid crystal display, plasma display and rear projection display; optical recording media represented by optical magnetic disk, read-only type optical disks such as CD•LD•DVD, phase transition type optical disk such as PD and hologram recording; photolithography-related members for production of semiconductors such as photoresist, photomask, pellicle and reticule; protection covers for light emitters such as halogen lamp, fluorescent lamp and incandescent lamp; and sheet or film for adhering to the above-mentioned articles.

The composition of the present invention is also effectively applied as a sealing agent on the following articles.

Photo-semiconductor, i.e. light emission devices such as LED; photodetectors such as photo transistor, photo diode and CCD; and semiconductor devices (photo-semiconductor device) such as EPROM.

Further the composition of the present invention is also effective as an adhesive when applied to articles in the form mentioned below.

Tape and substrate for a carrier of semiconductor device, lead frame, wiring board and wiring sheet such as printed circuit board and module board, and further a surface layer of a substrate for package and a surface of interlayer insulation.

EXAMPLES

The present invention is then explained by means of Examples and Synthesis Examples, but is not limited to those Examples.

The methods of measuring various physical properties and parameters used in the present invention are collectively explained below.

(1) NMR

Measuring equipment of NMR: available from BRUCKER CO., LTD.

Measuring conditions of $^1$H-NMR: 300 MHz (tetramethylsilane=0 ppm)

Measuring conditions of $^{19}$F-NMR: 282 MHz (trichlorofluoromethane=0 ppm)

(2) IR Analysis

Measuring is carried out at room temperature with a Fourier-transform infrared spectrophotometer 1760X available from Perkin Elmer Co., Ltd.

(3) Fluorine Content

The fluorine content (% by mass) is obtained by burning 10 mg of a sample by an oxygen flask combustion method, absorbing cracked gas in 20 ml of de-ionized water and then measuring a fluorine ion concentration in the fluorine ion-containing solution through fluoride-ion selective electrode method (using a fluorine ion meter model 901 available from Orion).

Example 1

Synthesis of Fluorine-Containing Allyl Ether Monomer Having Silicon Alkoxide

Into a 100 ml four-necked glass flask equipped with a stirrer and a thermometer were poured 20.0 g of perfluoro-(1,1,9,9-tetrahydro-2,5-bistrifluoromethyl-3,6-dioxanonenol):

10.0 g of γ-isocyanatepropyltrimethoxysilane (a ratio to perfluoro-[1,1,9,9-tetrahydro-2,5-bistrifluoromethyl-3,6-dioxanonenol]: 1.0 e.q.), 20 ml of tetrahydrofuran (THF) as a reaction solvent, and 0.01 g of di-n-butyltin laurate (a ratio to γ-isocyanatepropyltrimethoxysilane:0.10 mass %), followed by reaction with stirring at 45° C. for two hours. After completion of the reaction, the reaction solvent was distilled off with an evaporator, and IR analysis was carried out.

Since —OH group of perfluoro-[1,1,9,9-tetrahydro-2,5-bistrifluoromethyl-3,6-dioxanonenol] disappeared and a urethane bond (—OCONH—) was produced and also since an absorption peak derived from a silicon alkoxide (—SiOR—) was observed, the obtained reaction product was a fluorine-containing allyl ether monomer:

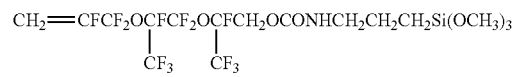

having silicon alkoxide. An IR chart is shown in FIG. 1.

Example 2

Synthesis of Polymer Comprising Fluorine-Containing Allyl Ether Having Silicon Alkoxide Into a 100 ml four-necked glass flask equipped with a stirrer and a thermometer were poured 20.1 g of the fluorine-containing allyl ether monomer having silicon alkoxide and obtained in Example 1, 20.4 g of perfluoro-(1,1,9,9-tetrahydro-2,5-bistrifluoromethyl-3,6-dioxanonenol):

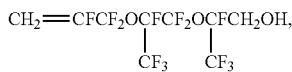

and 21.2 g of 8.0% by weight perfluorohexane solution of:

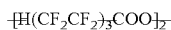

and after sufficiently replacing the inside of the flask with nitrogen, stirring was carried out at 20° C. for 24 hours in a nitrogen gas stream, and a highly viscose solid was produced.

The obtained solid was dissolved in diethyl ether and poured into perfluorohexane, followed by separation and vacuum drying to obtain 35.2 g of a colorless transparent polymer.

According to $^{19}$F-NMR analysis, $^1$H-NMR analysis and IR analysis, this polymer was a copolymer comprising a fluorine-containing allyl ether having OH group and a fluorine-containing allyl ether having —Si(OR)$_3$ group in a percent by mole ratio of 50:50.

Also according to GPC analysis using tetrahydrofuran (THF) as a solvent, a number average molecular weight of the polymer was 9,000, and a weight average molecular weight thereof was 22,000.

Example 3

Synthesis of Curable Fluorine-Containing Polymer Having Silicon Alkoxide and α-fluoroacryloyl Group Into a 200 ml four-necked flask equipped with a reflux condenser, a thermometer, a stirrer and a dropping funnel were poured 80 ml of diethyl ether, 5.0 g of the polymer containing fluorine-containing allyl ether having silicon alkoxide and obtained in Example 2, and 1.0 g of pyridine, followed by cooling to 5° C. or lower with ice.

While stirring in a nitrogen gas stream, a solution prepared by dissolving 1.0 g of α-fluoroacrylic acid fluoride: CH$_2$=CFCOF in 20 ml of diethyl ether was further added dropwise over about 30 minutes.

After completion of the addition, the temperature of the mixture was increased to room temperature, and stirring was continued for another 4.0 hours.

The ether solution after the reaction was poured into the dropping funnel, and after repeating washing with water, 2% hydrochloric acid solution, 5% NaCl solution and then water, was dried with anhydrous magnesium sulfate, and then the ether solution was separated by filtration.

According to $^{19}$F-NMR analysis, this ether solution was a copolymer comprising a fluorine-containing allyl ether having OCOCF=CH$_2$ group, a fluorine-containing allyl ether having OH group, and a fluorine-containing allyl ether having —Si(OR)$_3$ group in a percent by mole ratio of 40:10:50.

Figure 2:
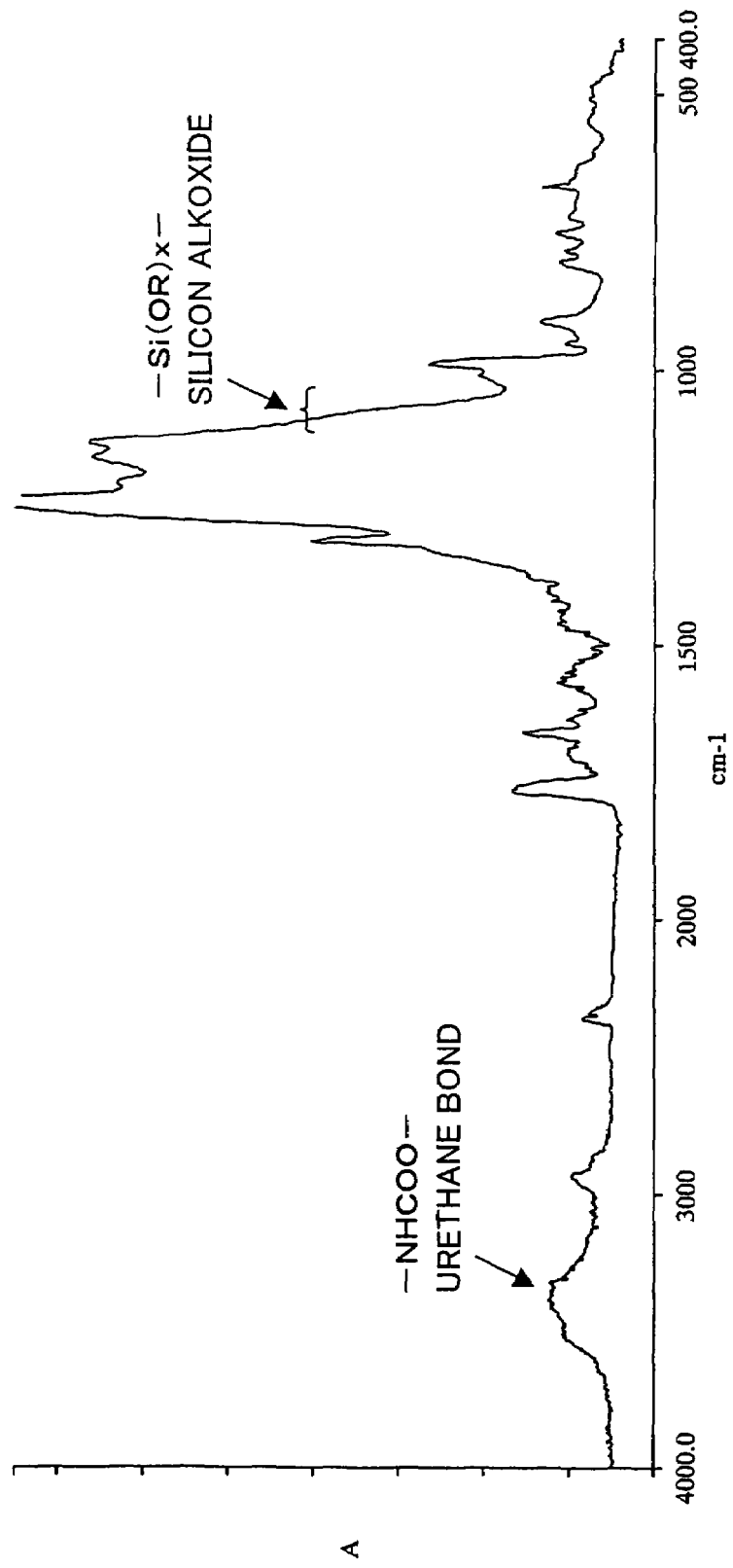
[FIG. 2] An IR chart of a curable fluorine-containing polymer which has a silicon alkoxide and α-fluoroacryloyl group and is synthesized in Example 3.

The obtained copolymer was coated on a silicon wafer, and formed into a cast film at room temperature. According to IR analysis of the cast film, an absorption of carbon-carbon double bond was observed at 1,661 cm$^{-1}$, an absorption of C=O group, at 1,770 cm$^{-1}$, and an absorption of Si(OCH$_3$)$_3$ group, at 1,100 cm$^{-1}$. An IR chart is shown in FIG. 2.

Example 4

(1) Preparation of Fluorine-Containing Resin Composition for Coating

To the curable fluorine-containing polymer (ether solution) having silicon alkoxide and α-fluoroacryloyl group and obtained in Example 3 was added methyl isobutyl ketone (MIBK), and then ether was distilled off with an evaporator to adjust the polymer concentration to 3.75% by weight.

To 10 g of the obtained polymer solution was added 1.7 g of a solution prepared by dissolving 2-methyl-1-[4-(methylthio)phenyl]-2-morpholinopropane-1-one as an active energy curing initiator in MIBK in a concentration of 1% by weight.

Example 5

(1) Preparation of Fluorine-Containing Resin Composition for Coating

A fluorine-containing resin composition for coating containing no silicon alkoxide was prepared in the same manner as in Example 4 except that the fluorine-containing allyl ether having —Si(OR)$_3$ group was not contained in the fluorine-containing resin composition prepared by means of Examples 2 to 4.

(2) Production of Laminated Article

The above-mentioned coating composition was applied to an un-coated PET film subjected to anti-glaring treatment with an applicator, and dried at 25° C. for five minutes.

(Light Irradiation)

The dried coating film was irradiated with ultraviolet light at an intensity of 3,000 mJ/cm$^2$U at room temperature using a high pressure mercury lamp.

(3) Measurement of Refractive Index of Curable Fluorine-Containing Polymer

The 3.75% MIBK solution of the curable fluorine-containing polymer (the polymer solution before adding the curing catalyst in the above-mentioned (1) of Examples 4 and 5) was coated on a PET film with an applicator so that a coating thickness after the drying became about 100 μm. After drying at 50° C. for 10 minutes, an obtained cast film was peeled from the PET film, and a refractive index thereof was measured using an Abbe's refractometer at 25° C. with light having a wavelength of 550 nm. The results are shown in Table 1.

(4) Measurement of Refractive Index of Cured Film

The coating compositions prepared in the above-mentioned (1) of Examples 4 and 5 were coated on an aluminum foil with an applicator so that a coating thickness became about 100 μm, followed by drying at 50° C. for 10 minutes. After the dried coating film was subjected to irradiation of 1 ight in the same manner as in (2) above, the aluminum foil was molten with diluted hydrochloric acid to make a sample film. A refractive index of the obtained cured film was measured in the same manner as in (3) above. The results are shown in Table 1.

(5) Evaluation of Physical Properties of Laminated Article

The following physical properties of the laminated article obtained in (2) above were evaluated. The results are shown in Table 1.

(5-5) Measurement of Reflectance of One Side of Film

A PET film provided with the laminated article was set on a thin film reflectance meter F-20 (available from Filmetrics Co.), and a reflectance was measured with light having a wavelength of 550 nm.

Comparative Example 1

A one side reflection of an un-coated PET film subjected to anti-glaring treatment was measured, and the results thereof are shown in Table 1.

TABLE 1

|  | Example 4 | Example 5 | Com. Ex. 1 |
|---|---|---|---|
| Substrate film | Anti-glare PET | Anti-glare PET | Anti-glare PET |
| Curable fluorine-containing polymer | Example 3 |  | Un-coated |
| Content of —O(C=O)CF=CH$_2$ group (% by mole) | 40 | 50 |  |
| Solvent | MIBK | MIBK |  |
| Concentration of polymer (% by weight) | 3.75 | 3.75 |  |
| Active energy curing initiator | Curing initiator 1 | Curing initiator 1 |  |
| Ratio to polymer (% by weight) | 3 | 3 |  |
| Amount of ultraviolet light (mJ/cm) | 4200 | 4200 |  |
| Refractive index |  |  |  |
| Before curing | 1.380 | 1.367 |  |
| After curing | 1.387 | 1.375 |  |
| Dry to touch | ○ | ○ | Un-coated |
| Solvent resistance | ○ | X |  |
| Abrasion resistance | ○ | X |  |
| Reflectance on one side of film (%) | 4.82 | 4.70 | 8.00 |

Curing initiator 1: 2-Methyl-1-[4-(methylthio)phenyl]-2-morpholinopropane-1-one (5-1) Dry to Touch Tackiness was evaluated by touching with fingers according to JIS K4500.

The evaluation is made by:

○: There is no tackiness.

X: There is tackiness.

(5-2) Pencil Hardness

Measured according to JIS K5400.

(5-3) Solvent Resistance

After the surface of the coating film is rubbed with a cotton cloth impregnated with acetone, condition (dissolved or peeled) of the coating film surface is evaluated.

When there is no change, it is evaluated as ○, and when there is dissolution or peeling, it is evaluated as X.

(5-4) Abrasion Resistance Test

A cotton cloth (BEMCOT (Registered trademark) M-3 available from Asahi Chemical Co., Ltd.) is fitted to a rubbing tester, and the laminated article is rubbed by 100 rubbing cycles at a load of 100 gf/cm². Then the condition of the film is observed.

The evaluation is made as follows.

○: There is no change.

Δ: A flaw is found partly.

X: There is a portion where a film is peeled and a substrate is seen.

INDUSTRIAL APPLICABILITY

The present invention can provide a material which is free from fading into white due to surface scattering while maintaining anti-glaring property and is useful as a laminated article having excellent adhesion and practical low reflection.

The invention claimed is:

1. A curable fluorine-containing polymer having a hydrolyzable metal alkoxide moiety which has a number average molecular weight of from 500 to 1,000,000 and is represented by the formula (2):

(2)

wherein the structural unit M is a structural unit derived from a fluorine-containing ethylenic monomer having a hydrolyzable metal alkoxide moiety and represented by the formula (M):

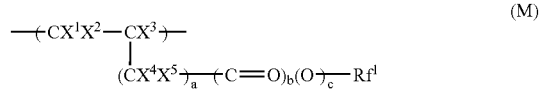
(M)

in which $X^1$ and $X^2$ are the same or different, and each is H or F; $X^3$ is H, F, $CH_3$ or $CF_3$; $X^4$ and $X^5$ are the same or different, and each is H, F or $CF_3$; $Rf^1$ is represented by the formula:

—D—Ry wherein —D— is a fluoroether unit represented by the formula (D):

$-(O-R)_{\overline{n}}$ or $-(R-O)_{\overline{n}}$ (D)

in which n is an integer of 1 to 20; R is at least one selected from fluorine-containing divalent alkylene groups having 1 to 5 carbon atoms where at least one of hydrogen atoms is replaced by fluorine atom, and R may be the same or different when n is not less than two; Ry is a hydrocarbon group having 1 to 39 carbon atoms where a part or the whole of hydrogen atoms are replaced by fluorine atoms or a hydrocarbon group having 1 to 99 carbon atoms and ether bond where a part or the whole of hydrogen atoms are replaced by fluorine atoms, which is an organic group in which one to three of hydrogen atoms are replaced by $Y^1$ where $Y^1$ is a functional group having, at its end, at least one hydrolyzable metal alkoxide moiety having 1 to 50 carbon atoms; a is 0 or an integer of 1 to 3; b and c are the same or different, and each is 0 or 1, the structural unit N is a structural unit derived from a fluorine-containing ethylenic monomer and represented by the formula (N):

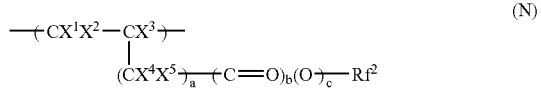  (N)

in which $X^1$ and $X^2$ are the same or different, and each is H or F; $X^3$ is H, F, $CH_3$ or $CF_3$; $X^4$ and $X^5$ are the same or different, and each is H, F or $CF_3$; $Rf^2$ is a fluorine-containing alkyl group having 1 to 40 carbon atoms or a fluorine-containing alkyl group having 2 to 100 carbon atoms and ether bond, which is an organic group in which 1 to 3 hydrogen atoms are replaced by $Y^2$ where $Y^2$ is a monovalent organic group having 2 to 10 carbon atoms and having, at its end, an ethylenic carbon-carbon double bond; a is 0 or an integer of 1 to 3; b and c are the same or different, and each is 0 or 1, the structural unit A is a structural unit derived from a monomer being copolymerizable with the fluorine-containing ethylenic monomers providing the structural units represented by the formulae (M) and (N), and the structural units M, N and A are contained in amounts of from 0.1 to 100% by mole, from 0 to 99.9% by mole and from 0 to 99.9% by mole, respectively.

2. The curable fluorine-containing polymer of claim 1, wherein at least one of $Y^1$ bonded to an end of $Rf^1$.

3. The curable fluorine-containing polymer of claim 1, wherein in the formula (2), the structural unit M is a structural unit M1 derived from a fluorine-containing ethylenic monomer and represented by the formula (M1):

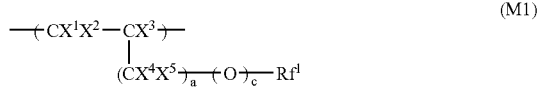  (M1)

wherein $X^1$, $X^2$, $X^3$, $X^4$, $X^5$, $Rf^1$, a and c are as defined above.

4. The curable fluorine-containing polymer of claim 1, wherein in the formula (2), the structural unit M is a structural unit M2 derived from a fluorine-containing ethylenic monomer and represented by the formula (M2):

  (M2)

wherein $Rf^1$ is as defined above.

5. The curable fluorine-containing polymer of claim 1, wherein in the formula (2), the structural unit M is a structural unit M3 derived from a fluorine-containing ethylenic monomer and represented by the formula (M3):

  (M3)

wherein $Rf^1$ is as defined above.

6. The curable fluorine-containing polymer of claim 1, wherein Ry is a group represented by the formula (Ry):

  (Ry)

wherein $Ry^1$ is an organic-inorganic complex radical represented by the formula:

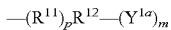

where p is 0 or 1; m is an integer of 1 to 3; $R^{11}$ is —CONH—; $R^{12}$ is a di-, tri- or tetra-valent hydrocarbon group having 1 to 39 carbon atoms where a part or the whole of hydrogen atoms are replaced by fluorine atoms or a di-, tri- or tetra-valent hydrocarbon group having 1 to 99 carbon atoms and ether bond where a part or the whole of hydrogen atoms are replaced by fluorine atoms; $Y^{1a}$ is a functional group represented by the formula:

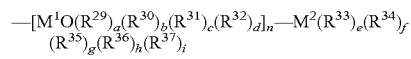

where $M^1$ and $M^2$ are the same or different and each is a di-, tri-, tetra-, penta- or hexa-valent metal atom; a, b, c and d are 0 or 1, and a+b+c+d+2 is equal to the number of valences of the metal atom $M^1$; e, f, g, h and i are 0 or 1, and e+f+g+h+i+1 is equal to the number of valences of the metal atom $M^2$; $R^{29}$, $R^{30}$, $R^{31}$, $R^{32}$, $R^{33}$, $R^{34}$, $R^{35}$, $R^{36}$ and $R^{37}$ are the same or different and each is an organic group represented by the formula: $OR^{38}$ or $R^{38}$ where $R^{38}$ is hydrogen atom or a hydrocarbon group having 1 to 10 carbon atoms in which a part or the whole of hydrogen atoms may be replaced by fluorine atoms, and at least one of $R^{29}$, $R^{30}$, $R^{31}$, $R^{32}$, $R^{33}$, $R^{34}$, $R^{35}$, $R^{36}$ and $R^{37}$ is $OR^{38}$; n is 0 or an integer of 1 to 11.

7. A curable fluorine-containing resin composition comprising:
(a) the curable fluorine-containing polymer having a hydrolyzable metal alkoxide moiety of claim 1, and
(b) a curing agent.

8. A cured article obtained by curing the curable fluorine-containing resin composition of claim 7.

9. A curable fluorine-containing resin composition for coating comprising:
(a) the curable fluorine-containing polymer having a hydrolyzable metal alkoxide moiety of claim 1,
(b) a curing agent, and
(c) a solvent.

10. A cured coating film obtained by curing a coating film formed by applying the curable fluorine-containing resin composition for coating of claim 9.

* * * * *